United States Patent
Kapre et al.

(10) Patent No.: US 10,729,763 B2
(45) Date of Patent: *Aug. 4, 2020

(54) MIXTURES OF POLYSACCHARIDE-PROTEIN PEGYLATED COMPOUNDS

(71) Applicant: Inventprise, LLC, Redmond, WA (US)

(72) Inventors: Subhash V. Kapre, Redmond, WA (US); Anup K. Datta, Renton, WA (US)

(73) Assignee: Inventprise, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/593,282

(22) Filed: Oct. 4, 2019

(65) Prior Publication Data

US 2020/0030439 A1    Jan. 30, 2020

Related U.S. Application Data

(63) Continuation-in-part of application No. 16/004,743, filed on Jun. 11, 2018.

(60) Provisional application No. 62/517,905, filed on Jun. 10, 2017.

(51) Int. Cl.
| | | |
|---|---|---|
| *A61K 39/385* | (2006.01) | |
| *A61K 39/09* | (2006.01) | |
| *A61K 39/00* | (2006.01) | |

(52) U.S. Cl.
CPC .......... *A61K 39/385* (2013.01); *A61K 39/092* (2013.01); *A61K 2039/6068* (2013.01); *A61K 2039/627* (2013.01)

(58) Field of Classification Search
None
See application file for complete search history.

(56) References Cited

U.S. PATENT DOCUMENTS

| | | | |
|---|---|---|---|
| 4,673,574 | A | 6/1987 | Anderson |
| 4,686,102 | A | 8/1987 | Ritchey et al. |
| 4,902,506 | A | 2/1990 | Anderson et al. |
| 5,360,897 | A | 11/1994 | Anderson et al. |
| 5,371,197 | A | 12/1994 | Marburg et al. |
| 5,565,204 | A | 10/1996 | Kuo et al. |
| 5,623,057 | A | 4/1997 | Marburg et al. |
| 5,681,570 | A | 10/1997 | Yank et al. |
| 5,807,553 | A | 9/1998 | Malcolm |
| 5,847,112 | A | 12/1998 | Kniskern et al. |
| 5,849,301 | A | 12/1998 | Lees |
| 5,866,132 | A | 2/1999 | Malcolm |
| 5,965,714 | A | 10/1999 | Ryall |
| 6,132,723 | A | 10/2000 | Malcolm |
| 6,177,085 | B1 | 1/2001 | Yank et al. |
| 6,224,880 | B1 | 5/2001 | Chan et al. |
| 6,656,472 | B1 | 12/2003 | Chong et al. |
| 6,863,893 | B2 | 3/2005 | Wizemann et al. |
| 7,018,637 | B2 | 3/2006 | Chong et al. |
| 7,435,421 | B2 | 10/2008 | Wizemann et al. |
| 7,501,132 | B2 | 3/2009 | Ades et al. |
| 7,524,821 | B2 | 4/2009 | Wang et al. |
| 7,709,001 | B2 | 5/2010 | Hausdorff et al. |
| 7,862,823 | B1 | 1/2011 | Leroy |
| 7,955,605 | B2 | 6/2011 | Prasad |
| 8,007,807 | B2 | 8/2011 | Borkowski |
| 8,029,798 | B2 | 10/2011 | Leroy |
| 8,048,432 | B2 | 11/2011 | Lee et al. |
| 8,173,135 | B2 | 5/2012 | Lee |
| 8,226,959 | B2 | 7/2012 | Gibson et al. |
| 8,246,964 | B2 | 8/2012 | Beninati et al. |
| 8,361,477 | B2 | 1/2013 | Borkowski |
| 8,444,992 | B2 | 5/2013 | Borkowski |
| 8,465,749 | B2 | 6/2013 | Lee et al. |
| 8,481,054 | B2 | 7/2013 | Nahm et al. |
| 8,557,250 | B2 | 10/2013 | Lee |
| 8,575,319 | B2 | 11/2013 | Timmerman |
| 8,603,484 | B2 | 12/2013 | Prasad |

(Continued)

OTHER PUBLICATIONS

Henrichsen 1995 (Six Newly Recognized Types of *Streptococcus pneumoniae* Journal of Clinical Microbiology 33(10):2759-2762) (Year: 1995).*
Song et al. 2011 (Comparison of Capsular Genes of *Streptococcus pneumoniae* Serotype 6A, 6B, 6C, and 6D isolates; Journal of Clinical Microbiology; 49(5):1758-1764) (Year: 2011).*
International Search Report and Preliminary Opinion for Application No. PCT/US2018/36868 dated Oct. 25, 2018.

* cited by examiner

*Primary Examiner* — Mary Maille Lyons
(74) *Attorney, Agent, or Firm* — Remenick PLLC

(57) ABSTRACT

The disclosure describes compositions containing PEGylated compounds using linkers, bivalent polysaccharide covalent PEG compounds, and methods of bivalent polysaccharide-PEG compounds in the development of multivalent vaccines. PEGylated conjugation of capsular polysaccharides to carrier proteins is carried out using homo-bifunctional and/or hetero-bifunctional linkers of specific lengths. Incorporation of bifunctional PEG linkers induces higher titers of functional antibodies with high avidity, eliciting higher immunologic memory, and reduced carrier protein effect. This provides immunochemically cross-reactive capsular polysaccharides wherein one or more cross-reactive capsular polysaccharides are covalently PEG compounded sequentially or concurrently to carrier protein using bifunctional linkers bearing the same or different functional groups. Such a linker and the size of the capsular polysaccharides provides an effective multivalent vaccine with high antibody titers and a reduced carrier effect, with a reduction in the content of the capsular polysaccharide and protein per dose of vaccine which reduces reactogenicity.

36 Claims, 6 Drawing Sheets

(56) References Cited

U.S. PATENT DOCUMENTS

| | | |
|---|---|---|
| 8,642,048 B2 | 2/2014 | Ades et al. |
| 8,652,480 B2 | 2/2014 | Yuan et al. |
| 8,703,148 B2 | 4/2014 | Biemans et al. |
| 8,753,649 B2 | 6/2014 | Lee et al. |
| 8,784,826 B2 | 7/2014 | Borkowski |
| 8,795,689 B2 | 8/2014 | Crinean |
| 8,808,707 B1 | 8/2014 | Siber et al. |
| 8,808,708 B2 | 8/2014 | Hausdorff et al. |
| 8,815,254 B2 | 8/2014 | Biemans et al. |
| 8,895,024 B2 | 11/2014 | Hausdorff et al. |
| 8,933,218 B2 | 1/2015 | Biemans et al. |
| 8,999,697 B2 | 4/2015 | Yuan et al. |
| 9,095,567 B2 | 8/2015 | Khandke et al. |
| 9,107,872 B2 | 8/2015 | Biemans et al. |
| 9,173,931 B2 | 11/2015 | Jessouroun et al. |
| 9,175,033 B2 | 11/2015 | Lee |
| 9,198,976 B2 | 12/2015 | Lee et al. |
| 9,205,143 B2 | 12/2015 | Davis et al. |
| 9,399,060 B2 | 7/2016 | Hausdorff et al. |
| 9,474,795 B2 | 10/2016 | Lee et al. |
| 9,475,804 B2 | 10/2016 | Wightman |
| 9,480,736 B2 | 11/2016 | Hausdorff et al. |
| 9,492,559 B2 | 11/2016 | Emini et al. |
| 9,499,593 B2 | 11/2016 | Malley et al. |
| 9,517,274 B2 | 12/2016 | Gu et al. |
| 9,610,339 B2 | 4/2017 | Biemans et al. |
| 9,610,340 B2 | 4/2017 | Biemans et al. |
| 9,669,084 B2 | 6/2017 | Siber et al. |
| 9,675,681 B2 | 6/2017 | Yuan et al. |
| 9,778,266 B2 | 10/2017 | Nahm et al. |
| 9,884,113 B2 | 2/2018 | Biemans et al. |
| 9,902,724 B2 | 2/2018 | Wightman |
| 9,950,054 B2 | 4/2018 | Gu et al. |
| 9,981,035 B2 | 5/2018 | Hausdorff et al. |
| 9,981,045 B2 | 5/2018 | Prasad |
| 2001/0048929 A1 | 12/2001 | Chong et al. |
| 2002/0094338 A1 | 7/2002 | Jonsdottir |
| 2003/0099672 A1 | 5/2003 | Schultz |
| 2003/0138447 A1 | 7/2003 | Wizemann et al. |
| 2003/0147922 A1 | 8/2003 | Capiau et al. |
| 2005/0118199 A1 | 6/2005 | Esser et al. |
| 2005/0142145 A1 | 6/2005 | Wizemann et al. |
| 2005/0159341 A1 | 7/2005 | Wang et al. |
| 2005/0214329 A1 | 9/2005 | Laferriere et al. |
| 2005/0226891 A1 | 10/2005 | Ades et al. |
| 2006/0051361 A1 | 3/2006 | Laferriere et al. |
| 2006/0093626 A1 | 5/2006 | Capiau et al. |
| 2006/0140981 A1 | 6/2006 | Jonsdottir |
| 2006/0228380 A1 | 10/2006 | Hausdorff et al. |
| 2007/0110762 A1 | 5/2007 | Jessouroun et al. |
| 2007/0141084 A1 | 6/2007 | Lee et al. |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2007/0253985 A1 | 11/2007 | Look et al. |
| 2008/0260773 A1* | 10/2008 | Del Giudice ........ A61K 39/095 424/196.11 |
| 2008/0286838 A1 | 11/2008 | Yuan et al. |
| 2009/0017060 A1 | 1/2009 | Timmerman |
| 2009/0092632 A1 | 4/2009 | Lee |
| 2009/0130137 A1 | 5/2009 | Hausdorff et al. |
| 2009/0136548 A1 | 5/2009 | Ades et al. |
| 2009/0317412 A1* | 12/2009 | Alexander ........... A61K 31/715 424/185.1 |
| 2010/0034847 A1 | 2/2010 | Borkowski |
| 2010/0074922 A1 | 3/2010 | Biemans et al. |
| 2010/0143414 A1 | 6/2010 | Nahm et al. |
| 2010/0158953 A1 | 6/2010 | Crinean |
| 2010/0183662 A1 | 7/2010 | Biemans et al. |
| 2010/0209450 A1 | 8/2010 | Biemans et al. |
| 2010/0239604 A1 | 9/2010 | Biemans et al. |
| 2010/0303852 A1 | 12/2010 | Biemans et al. |
| 2010/0316666 A1 | 12/2010 | Hausdorff et al. |
| 2010/0322959 A1 | 12/2010 | Biemans et al. |
| 2011/0071279 A1 | 3/2011 | Hausdorff et al. |
| 2011/0076301 A1 | 3/2011 | Beninati et al. |
| 2011/0091506 A1 | 4/2011 | Gibson et al. |
| 2011/0117123 A1 | 5/2011 | Leroy |
| 2011/0159030 A1 | 6/2011 | O'Hagan |
| 2011/0195086 A1 | 8/2011 | Caulfield |
| 2011/0201791 A1* | 8/2011 | Prasad ................ A61P 11/00 530/403 |
| 2011/0311574 A1 | 12/2011 | Borkowski |
| 2012/0076817 A1 | 3/2012 | Lee et al. |
| 2012/0135037 A1 | 5/2012 | Mizel et al. |
| 2012/0195922 A1 | 8/2012 | Lee |
| 2012/0231086 A1 | 9/2012 | Killen et al. |
| 2012/0237542 A1 | 9/2012 | Hausdorff et al. |
| 2012/0321658 A1 | 12/2012 | Biemans et al. |
| 2013/0004535 A1 | 1/2013 | Borkowski |
| 2013/0004536 A1 | 1/2013 | Borkowski |
| 2013/0072881 A1 | 3/2013 | Khandke et al. |
| 2013/0315958 A1 | 11/2013 | Nahm et al. |
| 2013/0337004 A1 | 12/2013 | Lee et al. |
| 2014/0010843 A1 | 1/2014 | Biemans et al. |
| 2014/0044748 A1 | 2/2014 | Lee |
| 2014/0099337 A1 | 4/2014 | Davis et al. |
| 2014/0154286 A1 | 6/2014 | Malley et al. |
| 2014/0227317 A1 | 8/2014 | Wightman |
| 2014/0314805 A1 | 10/2014 | Hausdorff et al. |
| 2014/0322258 A1 | 10/2014 | Lee et al. |
| 2014/0322263 A1 | 10/2014 | Siber et al. |
| 2014/0348868 A1 | 11/2014 | Donati et al. |
| 2014/0363463 A1 | 12/2014 | Yuan et al. |
| 2015/0038685 A1 | 2/2015 | Hausdorff et al. |
| 2015/0079132 A1 | 3/2015 | Maisonneuve et al. |
| 2015/0165017 A1 | 6/2015 | Yuan et al. |
| 2015/0202309 A1 | 7/2015 | Emini et al. |
| 2015/0216996 A1 | 8/2015 | Gu et al. |
| 2015/0231270 A1 | 8/2015 | Prasad |
| 2015/0265702 A1 | 9/2015 | Biemans et al. |
| 2015/0328328 A1 | 11/2015 | Han et al. |
| 2015/0344530 A1 | 12/2015 | Kapre |
| 2016/0136256 A1 | 5/2016 | Lee et al. |
| 2016/0158345 A1 | 6/2016 | Hausdorff et al. |
| 2016/0324948 A1 | 11/2016 | Gu et al. |
| 2016/0324949 A1 | 11/2016 | Han et al. |
| 2017/0021006 A1 | 1/2017 | Watson et al. |
| 2017/0021008 A1 | 1/2017 | Drew |
| 2017/0037045 A1 | 2/2017 | Wightman |
| 2017/0143821 A1 | 5/2017 | Porro |
| 2017/0224804 A1 | 8/2017 | Gu et al. |
| 2017/0246313 A1 | 8/2017 | Gill et al. |
| 2017/0252423 A1 | 9/2017 | Siber et al. |
| 2018/0136224 A1 | 5/2018 | Nahm et al. |
| 2018/0186792 A1 | 7/2018 | Wightman |
| 2018/0221467 A1 | 8/2018 | Gu et al. |
| 2018/0250390 A1 | 9/2018 | Hausdorff et al. |
| 2018/0256739 A1 | 9/2018 | Prasad |
| 2018/0353591 A1 | 12/2018 | Kapre et al. |
| 2019/0000953 A1 | 1/2019 | Gu et al. |

THIOLATION OF CRM197 WITH IMINOTIOLENE

TRAUT'S REAGENT  PRIMARY AMINE  MODIFICATION PRODUCING A
(2-IMINOTHILANE.HCl)  TERMINAL SULFHYDRYL GROUP

MIXTURES OF POLYSACCHARIDE-PROTEIN PEGYLATED COMPOUNDS

REFERENCE TO RELATED APPLICATIONS

This application is a continuation-in-part of U.S. application Ser. No. 16/004,743, filed Jun. 11, 2018, which is pending, and which claims priority to U.S. Provisional Application No. 62/517,905 filed Jun. 10, 2017, the entirety of each of which is specifically incorporated by reference.®

BACKGROUND

1. Field of the Invention

The present invention is directed to complexes comprising multivalent compounds, immunogenic compositions, and vaccines comprising carrier protein coupled to bacterial capsular polysaccharides and uses thereof. In particular, compositions of the invention comprise monovalent and bivalent and/or multivalent bacterial capsular PEGylated polysaccharide-protein compounds, wherein the bacterial capsular polysaccharides and oligosaccharides are derived from serotypes of *Streptococcus pneumoniae*. The carrier protein is coupled to PEG which in turn is coupled to bacterial capsular polysaccharides, through mono functional as well as bi-functional PEG linkers, preferably of defined lengths and the mono-functional or bi-functional linkers may be homo-mono-functional, homo-bi-functional, hetero-mono-functional, or hetero-bifunctional.

Description of the Background

*Streptococcus pneumoniae* is a Gram-positive pathogen responsible for invasive pneumococcal diseases (IPDs) such as pneumonia, bacteremia, meningitis, and acute Otitis media. Pneumonia is the most common manifestation of invasive pneumococcal disease, whereas bacterial spread within the respiratory tract may result in middle-ear infection, sinusitis or recurrent bronchitis. Pneumococcus is encapsulated with a chemically linked polysaccharide which results in serotype specificity. At least 90 pneumococcal serotypes are known of which about 23 account for 90% of invasive diseases and capsular polysaccharide is a poor immunogen.

There are currently three PCV vaccines available on the global market: PREVNAR®, SYNFLORIX®, and PREV-NAR-13®. There is a need to address remaining unmet medical need for coverage of pneumococcal disease due to serotypes not found in PREVNAR-13® and potential for serotype replacement over time. here is a need for immunogenic compositions covering pathogenic serotypes and methodology that can be used to induce a uniform and high immune response against all serotypes including the additional *Streptococcus pneumoniae* serotypes in humans and in children less than two years old.

A capsular polysaccharide (CPS) is a key virulence determinant and generally insufficiently immunogenic to induce a T cell-dependent immune response in infants and children. Conjugation of a carrier protein to CPS can induce an immune response that undergoes class switching. Accordingly, a 7-valent (PCV-7, Pfizer Inc., USA), a 10-valent (Synflorox-10, GSK Vaccines) and a 13-valent pneumococcal conjugate vaccine (PCV-13, Pfizer Inc., USA) have been developed to efficiently prevent the incidence of IPDs. Reductive amination chemistry and cyanylation chemistry has been widely used to prepare the conjugate vaccines.

U.S. Pat. No. 9,492,559 discloses immunogenic compositions comprising conjugated capsular polysaccharide antigens and uses thereof. The immunogenic compositions disclosed include an 8, 9, 10, 11, 12, 13, 14, 15, 16, 17, 18, 19 or 20-valent pneumococcal conjugate composition. Also disclosed is a 7, 8, 9, 10, 11, 12, 13, 14, 15, 16, 17, 18, 19, 20, 21, 22, 73, 24 or 25-valent pneumococcal conjugate composition.

International Application Publication No. WO 2014/097099A2 discloses a glycol-conjugation process directed to several serotypes in addition to Preevnar-13 valent conjugates. New polysaccharide conjugates are added to formulation to increase efficacy of the vaccine.

U.S. Patent Application Publication No. 2011/023526 discloses a 15-valent pneumococcal polysaccharide-protein conjugate vaccine composition. This patent is directed to 15-valent conjugate vaccines made by adding two or more serotypes with currently available 1-3 vaccines.

International Application Publication No. WO 2016/207905 discloses multivalent pneumococcal conjugate vaccine. This application is directed to a 13 or greater valent conjugate vaccine and deletion of serotype 6A.

U.S. Patent Application Publication No. 2017/007713 discloses a linker containing ((2-oxoethyl) thio) with enhanced functionality.

International Application Publication No. WO 2014/092377 discloses a 13 valent composition wherein 12 serotypes were selected from the group consisting of serotypes 1, 3, 4, 5, 6A, 6B, 7F, 9V, 14, 18C, 19A, 19F, and 23F and one from 12 or 9N.

International Application Publication No. WO 2014/092378 discloses an immunogenic composition having 13 different polysaccharide-protein conjugates wherein each conjugate contained a capsular polysaccharide isolated from 12 serotypes selected from the group consisting of serotypes 1, 3, 4, 5, 6A, 6B, 7F, 9V, 14, 18C, 19A, 19F and 23F, and serotypes 22F or 33F.

Chinese Application Publication No. 101590224 discloses a 14-valent pneumococcal polysaccharide-protein conjugate vaccine containing serotypes 1, 2, 4, 5, 6A, 6B, 7F, 9N, 9V, 14, 18C, 19A, 19F and 23F.

Chinese Application Publication No. 104069488 discloses 14 valent polysaccharide protein conjugate wherein the 14 serotypes were 1, 4, 5, 6A, 6B, 7F, 9V, 14, 18C, 19A, 19F, 22F, 23F and 33F.

International Application Publication No. WO 2016207905 discloses a multivalent pneumococcal conjugate vaccine comprising conjugates of CRM197 and at least 14 capsular polysaccharides selected from serotypes 1, 3, 4, 5, 6B, 7F, 9N, 9V, 14, 15B, 18C, 19A, 19F, 22F, 23F and 33F. U.S. Pat. No. 8,192,746 disclosed a 15 valent immunogenic composition comprising capsular polysaccharides from serotypes 1, 3, 4, 5, 6A, 6B, 7F, 9V, 14, 18C, 19A, 19F, 22F, 23F, and 33F conjugated to CRM197.

International Application Publication No. WO 2013/191459 discloses a 15 valent composition comprising *S. pneumoniae* capsular polysaccharides form serotypes of 1, 2, 3, 4, 5, 6A, 6B, 7F, 9N, 9V, 14, 18C, 19A, 19F and 23F.

Chinese Application Publication No. 103656632 discloses multi valent pneumococcal capsular polysaccharide composition containing serotype 6A and at least one extra serotype selected from the group consisting of 1, 2, 3, 4, 5, 6B, 7F, 8, 9N, 10A, 11A, 12F, 14, 15B, 17F, 18C, 19A, 19F, 20, 22F, 23F and 33F which provided protection against 24 different pneumococci serotypes.

Chinese Application Publication No. 103656631 discloses a multivalent pneumococcus capsular polysaccharide-protein conjugate composition comprising capsular polysaccharides of pneumococcus of 24 different serotypes viz. 1, 2, 3, 4, 5, 6A, 6B, 7F, 8, 9N, 9V, 10A, 11A, 12F, 14, 15B, 17F, 18C, 19A, 19F, 20, 22F, 23F and 33F.

U.S. Patent Application Publication No. 2016/0324950 discloses immunogenic polysaccharide-protein conjugates comprising a capsular polysaccharide (CP) from *Streptococcus agalactiae*, also referred to as group B streptococcus (GBS), and a carrier protein, wherein the CP is selected from the group consisting of serotypes Ia, Ib, II, III, IV, V, VI, VII, VIII, and IX. This was meant for treatment of chronic diabetes mellitus, cancer, heart failure, neurologic, and urologic conditions. The carrier protein capsular polysaccharide conjugates varied.

U.S. Pat. No. 5,360,897 discloses immunogenic conjugate comprising reductive amination product of an intact capsular polymer of the bacterial pathogen *S. pneumoniae* having at least two carbonyl groups and a bacterial toxin or toxoid, said conjugate comprising a cross-linked conjugate in which there is a direct covalent linkage between the capsular polymer and the toxin or toxoid.

U.S. Pat. No. 7,862,823 describes a multivalent conjugate vaccine composition with at least two different carrier proteins.

U.S. Pat. No. 8,808,708 discloses a 13-valent immunogenic composition consisting of polysaccharide-protein conjugates where serotypes consist of 1, 3, 4, 5, 6A, 6B, 7F, 9V, 14, 18C, 19A, 19F and 23F, and wherein the carrier protein is CRMl97.

U.S. Patent Application Publication No. 2009/0017059 discloses an immunogenic composition where serotypes 19A and 19F were conjugated to different bacterial toxoids.

International Application Publication No. WO 2011/110241 describes pneumococcal conjugate immunogenic compositions or vaccines wherein different conjugation chemistries were used for different components of the immunogenic composition or vaccine. Reductive amination was used for the conjugation of at least one serotype and a conjugation other than reductive amination was used for the conjugation of a different serotypes. The conjugation method selected for different serotypes allowed each serotype to be presented using a conjugation method that allowed the best presentation of the saccharide epitope. Some pneumococcal saccharides conjugated well using reductive amination, whereas other pneumococcal saccharides were conjugated differently to allow the ring structure to remain unbroken and provide better results.

U.S. Pat. No. 7,955,605 discloses a process of making carrier protein polysaccharide conjugate consisting serotype 19A where the activated serotype 19A polysaccharide and carrier protein are suspended in dimethyl sulfoxide (DMSO) to form a conjugate.

U.S. Patent Application Publication No. 2010/0074922 discloses immunogenic composition containing 10 or more serotypes wherein 19F capsular saccharide was conjugated to diphtheria toxoid (DT), serotype 18C capsular saccharide is conjugated to tetanus toxoid and serotypes 1, 4, 5, 6B, 7F, 9V, 14 and 23F capsular saccharides are conjugated to Protein D from *Haemophilus influenza*.

U.S. Patent Application Publication No. 2010/0239604 discloses a composition comprising multivalent *S. pneumoniae* capsular saccharide conjugates wherein serotype 19A was conjugated to a first bacterial toxoid and 19F is conjugated to a second bacterial toxoid and 2-9 of the *S. pneumoniae* capsular saccharides are conjugated to protein D.

Apart from increasing the scope of protection by developing vaccines which will offer protection against larger number of serotypes, efforts were focused on developing newer methods of synthesis.

U.S. Pat. No. 7,709,001 describes a method of synthesis of carrier protein conjugate of capsular polysaccharide which consists of 1) reacting purified polysaccharide with a mild acid resulting in size reduction 2) reacting the polysaccharide of step 1 with an oxidizing agent in the presence of bivalent cations resulting in an activated polysaccharide; 3) compounding the activated polysaccharide with a carrier protein 4) reacting activated polysaccharide of step 3 and carrier protein with a reducing agent to form a polysaccharide-carrier protein conjugate; and 5) capping unreacted aldehydes in product of step 4 to yield an immunogenic polysaccharide-carrier protein conjugate.

International Application Publication No. WO 2014/097099 discloses a method of synthesizing a carrier protein conjugate, which involves a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups.

U.S. Patent Application Publication No. 2012/321658 discloses an immunogenic composition wherein serotypes 1,3, 19A and 19F linked to protein carriers either directly or indirectly through a chemistry other than reductive amination, and one or more different saccharides is/are selected from a second group consisting of serotypes 4, 5, 6A, 6B, 7F, 9V, 14, 18C and 23F which is/are linked to a protein carriers) by reductive amination.

Pneumococcal vaccines are based on 1) pneumococcal polysaccharide vaccine and 2) pneumococcal conjugate vaccines. PNEUMOVAX® marketed by Merck comprises of unconjugated polysaccharides belonging to serotypes 1, 2, 3, 4, 5, 6B, 7F, 8, 9N, 9V, 10A, 11A, 12F, 14, 15B, 17F, 18e, 19F, 19A, 20, 22F, 23F and 33F. Infants and young children respond poorly to most pneumococcal polysaccharides. Immunogenicity of poor immunogens is enhanced by conjugating with carrier proteins. Polysaccharide protein conjugate vaccines are made using capsular polysaccharides linked to protein carriers. The conjugate induces T cell dependent enhanced immune response against the specific serotype.

Conjugates are synthesized using various reagents, such as homo bifunctional, hetero bifunctional linkers of varying lengths. Three pneumococcal conjugate vaccines are available in market, PREVNAR®, SYNFLORIX®, and PREVNAR-13®. PREVNAR® is a heptavalent vaccine that contains the capsular polysaccharides from serotypes 4, 6B, 9Y, 14, 18C, 19F and 23F, each conjugated to a carrier protein designated CRM197. SYNFLORIX® is a deca-valent vaccine from GSK Biologicals that incorporates ten capsular polysaccharides conjugated to protein D from NTHi offering coverage against three additional pneumococcal strains, serotypes 1, 5 and 7F. PREVNAR-13® is a tri-deca-valent vaccine containing 13 capsular polysaccharide prepared from thirteen serotype of *Streptococcus pneumoniae* (1, 3, 4, 5, 6A, 6B, 7F, 9Y, 14, 18C, 19 A, 19F, and 23F) conjugated to a carrier protein designated CRM197.

Increasing microbial resistance to antibiotics and the increasing number of immunocompromised persons have necessitated the development of pneumococcal vaccines with even broader protection, which leads to development of multivalent vaccines effective against increasing number of serotypes especially for coverage of pneumococcal disease due to serotypes not found in PREVNAR-13®. The need for a specific serotype depends on the region and antibiotic resistance developed. Thus, U.S. Pat. No. 8,192,746 reports a multivalent immunogenic composition having 15 distinct polysaccharide-protein conjugates. Each conjugate consists of a capsular polysaccharide prepared from serotype of *Streptococcus pneumoniae* (1, 3, 4, 5, 6A, 6B, 7F, 9\1, 14, 18C, 19A, 19F, 22F, 23F, or 33F) conjugated to a carrier protein CRM197. There is a need for vaccines that induce an immune response against serotype 15B, 15C, and 15A.

With the current methods increasing number of polysaccharide antigens in the multivalent conjugate vaccine formulations, the carrier protein content increases. This increase leads to an increase of immune response to the carrier protein which can cause a systemic overload. This needs to be reduced. Also, there is a lowering of immune response as the serotypes increase, which needs to be increased.

Thus, there is a need to develop a pneumococcal vaccine that provides uniform protection against increasing number of serotypes, and a reduction of the immune response to the carrier protein. Also the immune response to individual serotypes is preferably not affected by an increase in the antigen number. In the development of multivalent vaccines that extend the immune stimulus for existing and additional serotypes, there is a need to work on all factors involved in the conventional established conjugation methods. In addition to offering suitable protection against increasing number of serotypes, there is also a need to develop methods to reduce carrier protein antibodies in spite of an increase in the number of serotypes.

SUMMARY OF THE INVENTION

The present invention overcomes the problems and disadvantages associated with current strategies and designs and provides new compositions and methods creating uniform high immune response and a decrease in the antibody response to the carrier protein. This is done by using PEGylation and by having the same PEG molecule connect with the polysaccharides as well as the carrier protein to avoid PEG overload. Also the PEG chosen is preferably below 1 KDa in molecular weight to avoid any PEG antibody generation.

One embodiment of the invention is directed to immunogenic complexes comprising a first group of monovalent capsular polysaccharides and a second group of bivalent or multivalent capsular polysaccharides wherein the first group of monovalent capsular polysaccharides comprise polysaccharides of *S. pneumoniae* serotypes 1, 2, 3, 4, 5, 6A, 6B, 6C, 6D, 7F, 8, 9V, 9N, 9A, 9B, 10A, 11A, 12F, 14, 15B, 15A, 15C, 17F, 18C, 19A, 19F, 20, 22F, 23F, 24F, 33F and 35B; and the second group of bivalent or multivalent capsular polysaccharides comprises polysaccharides of *S. pneumoniae* serotypes 6A/6B/6C/6D, *S. pneumoniae* serotypes 9V/9N/9A/9B, *S. pneumoniae* serotypes 15B/15A/15C, or *S. pneumoniae* serotypes 19A/19F, wherein the first group of monovalent capsular polysaccharides are each covalently coupled to a PEG linker and a first carrier protein, and the second group of bivalent or multivalent capsular polysaccharides are each covalently coupled to another PEG linker and another carrier protein. The multivalent *S. pneumoniae* vaccines comprising two groups of compounds, wherein group one comprises of compounding one bacterial capsular polysaccharide to a carrier protein using a linker with PEG in between to cause PEGylation of both components promoting increase of immunogenicity to the polysaccharides. and a decrease of immunogenicity to the carrier protein.

To further achieve a reduction in the quantity of the carrier, compounds of the disclosure involve one carrier protein molecule for two or more polysaccharides. To do this with PEGYlation, a suitable linker with PEG in between is used to connect to a specific amino acid group in the carrier protein which ensures unique compounding in a constant manner. This principle is followed with a second polysaccharides by making the PEG linker attach to different amino acids allowing both linkers to co-exist in a precise manner always creating uniformity. As this mechanism provides a precise attachment to a specific amino acid group in the protein, the method results in a consistent coupling with same ratios of polysaccharides to protein. Thus, one can use diverse polysaccharides and reduce antibody quantity per dose, lowering the immune response to carrier protein, but keeping the polysaccharide response equivalently or higher. For example, conjugating two micrograms of one serotype and also two micrograms of another polysaccharide would involve half the dose reducing both the polysaccharide quantity as well as carrier protein quantity without any reduction in the protective response.

This methodology is effective for cross reactive serotypes wherein reduction in quantity in a single dose would not reduce the total immune response which would happen if conventional patented and published methods were to be used. Preferably, group one compounds are composed of monovalent capsular polysaccharide compounds of one or more *S. Pneumoniae* serotypes from 1, 2, 3, 4, 5, 6A, 6B, 6C, 6D, 7F, 8, 9V, 9N, 9A, 9B, 10A, 11A, 12F, 14, 15A, 15B, 15C, 17F, 18C, 19A, 19F, 20, 22F, 23F, 24F, 33F and 35B. Group two compounds are composed of a bivalent or multivalent capsular polysaccharides compounds of cross reactive serotypes of one, two or more of *S. pneumoniae* serotypes 6A/6B/6C/6D, one, two or more of *S. pneumoniae* serotypes 9V/9N/9A/9B, one, two or more of *S. pneumoniae* serotypes 15B/15A/15C, or *S. pneumoniae* serotypes 19A/19F; and carrier proteins. Preferably, the second group constituting the multivalent *S. pneumoniae* vaccine compound comprises multivalent compounds of *S. pneumoniae* cross reactive serotypes wherein the compounds are unimolecular bivalent compounds derived from bacterial capsular polysaccharides.

The methods of this disclosure also create hetero bifunctional groups using other antigens not belonging to Pneumo group to avoid making another vaccine for immunization, such as compounding HIA polysaccharide and HIB polysaccharide to a common carrier protein.

Preferably, the complex comprises capsular polysaccharide of two immunologically cross-reactive serotypes connected to the same carrier protein sequentially or concurrently. Preferably monovalent bacterial capsular polysaccharide protein compounds of the first or second group are synthesized from native bacterial capsular polysaccharides with molecular weight ranges of about 10 KDa to about 50 KDa, about 30 KDa to about 100 KDa, or about 100 KDa to about 300 KDa.

Preferably, the bivalent capsular polysaccharide of two immunologically cross-reactive serotypes is represented by the formula PS1-PEG-CarrierProtein-PEG-PS2 and, also preferably, the compound comprises, for example, 6A-PEG-CRM197-PEG-6B Preferably the carrier protein comprises Tetanus Toxoid, Diphtheria Toxoid, CRM197, Tetanus Toxoid fragments (TTHc), *N. meningitidis* protein PorB, RSV virus proteins, *B. pertussis* proteins, Pertussis toxoid (PT), Adenylate cyclase Toxin (ACT), 69 KDa protein, Human Papilloma viral protein antigens, Human Papilloma virus VLP forms, Hepatitis B virus core antigen, Hepatitis B virus VLP forms, derivatives of HBsAg, or combinations thereof. Preferably a single dose of bivalent cross-reactive polysaccharide compound comprises less than 4 micrograms in comparison to monovalent compounds of the same two polysaccharide vaccines which would add up to about 4 micrograms or more.

Preferably, total carrier protein quantity in the multivalent compounded vaccine is significantly lower than the quantity used in the mono compounds of the individual polysaccharides of the same cross-reactive serotypes. Preferably, the vaccines of the present invention, the carrier protein amount being compounded to a bivalent cross-reactive polysaccharide has less protein per serotype in comparison to that of the monovalent compounds of two polysaccharides to one protein thereby reduce the carrier protein immune response generated by the latter vaccine compound Preferably total carrier protein content in the multivalent compounded vaccine is from 0.5 to about 0.7% by weight of the mono compounds of the individual polysaccharides of the same cross-reactive serotypes (which is 1:1 ratio between PS:Carrier Protein). Preferably, the vaccine further comprises at least one adjuvant selected from the group consisting of aluminum or an aluminum salt, calcium phosphate, a liposome of monophosphoryl lipid A (MPLA), saponin QS-21, and/or a potent TLR7/8 agonist. Preferably the at least one adjuvant comprises an aluminum adjuvant selected from the group consisting of aluminum phosphate, aluminum sulfate and aluminum hydroxide. Preferably the bacterial polysaccharides are selected from the group consisting of cross reacting two or more serotypes from different bacterial capsular polysaccharides and/or the bacterial polysaccharides comprise: S. pneumoniae and H. influenza type a, b serotypes; S. pneumoniae and Group B Streptococcus serotypes, H. influenza type a, b serotypes, or N. meningitis serotypes. Preferably the capsular polysaccharides comprise polysaccharides derived from Streptococcus pneumoniae, Haemophilus influenza, N. meningitis, Group B Streptococcus, or Moraxella catarrhalis lipo-oligosaccharides (LOS). Also preferably, the S. pneumoniae capsular polysaccharide is immunochemically cross-reactive with serotypes selected from the group consisting of 6A/6B/6C/6D; 9V/9A/9B.9N; 15A/15B; 19A/19F and similar types of cross reactive polysaccharides. Preferably, the capsular polysaccharide is derived from Haemophilus influenza serotypes a/b/c/d/e/f, non-typeable Haemophilus influenza (NTHi) polysaccharides, or Moraxella catarrhalis Lipooligosaccharides (LOS), or N. meningitis serotypes A, B, C, Y, W-135 or X, or Group B Streptococcus serotypes Ia, Ib, II, III, IV, V, VI, VII, VIII. IX and N, and N. meningitis serotypes A, C, Y, X, and W-135.

Another embodiment of the invention is directed to compound vaccines for the treatment or prevention of infection by Gram-positive and Gram-negative pathogens comprising a therapeutically effective amount of the compound vaccine of the invention and, optionally, a pharmacologically acceptable carrier. Preferably the capsular polysaccharides are derived from Haemophilus influenza, N. meningitis, Group B Streptococcus, N. meningitis, H. influenza, Moraxella catarrhalis lipo-oligosaccharides (LOS), and combination thereof.

Another embodiment of the invention is directed to methods for coupling polysaccharides to PEG and then the same PEG with carrier protein comprising: activating the polysaccharide; attaching a define length of PEG spacer arm of about 2.0 Å to about 40 Å to the activated polysaccharide; and attaching the activated polysaccharide attached to PEG spacer arm to a carrier protein. PEG acts as an unexpected booster to immune response to polysaccharides which also acts to reduce the response to the carrier protein. The result is a highly effective immunogenic complex with reduced detrimental effects.

Another embodiment of the invention is directed to methods coupling a carrier protein to PEG and then the PEG with polysaccharides comprising: activating the said carrier protein, reducing the carrier proteins disulfide to create sulfhydryl groups, preferably creating a sulfhydryl group using 2-iminothiolane (2-IT), SMPH like bi-functional PEG linker; attaching a defined length PEG spacer arm of about 4 Å to about 40 Å to the activated carrier protein; and then attaching the polysaccharide to a similar PEG spacer arm attached to activated carrier protein. Preferably the activated carrier protein is selected from cross-reactive material (CRM197) obtained or derived from C. diphtheria, or recombinant CRM197 obtained or derived from P. fluorescens or E. coli.

Another embodiment of the invention is directed to immunogenic complexes containing bifunctional PEG linkers that are is homo-bifunctional or hetero-bifunctional, such as combinations of one genus of polysaccharides as well as another genus of polysaccharides.

Another embodiment of the invention is directed to multivalent S. pneumoniae vaccine compound wherein carrier protein is cross-reactive material (CRM197) obtained from C. diphtheria, recombinant CRM197 obtained from P. fluorescens, or recombinant CRM197 obtained from E. coli.

Other embodiments and advantages of the invention are set forth in part in the description, which follows, and in part, may be obvious from this description, or may be learned from the practice of the invention.

DESCRIPTION OF THE INVENTION

Figure 1A:
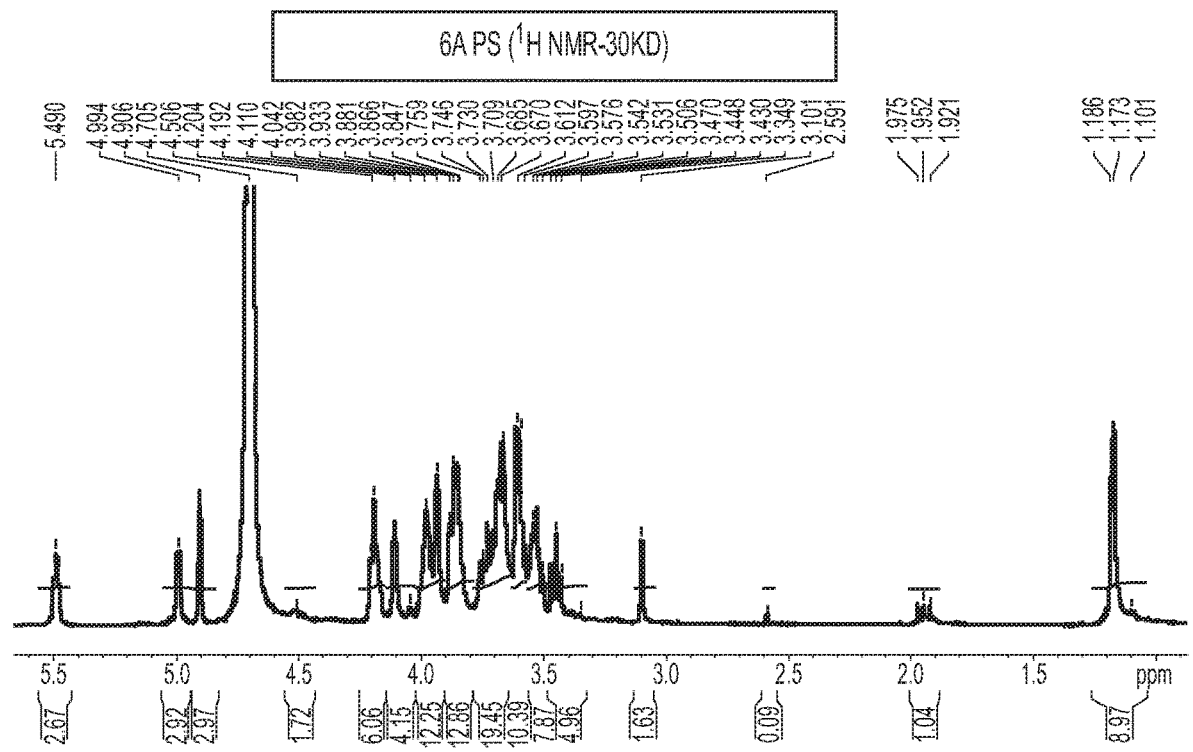
FIG. 1A Size reduced capsular polysaccharide of serotype 6A 1H-NMR spectra (500 MHz)-NMR data shows no loss of structural integrity compared to native PS.

*Streptococcus pneumoniae* is a Gram-positive bacterium which can cause diseases such as pneumonia, bacteraemia, meningitis, and acute Otitis media. Pneumococcus is encapsulated with a chemically linked polysaccharide which results in serotype specificity. At least 90 pneumococcal serotypes are known of which about 23 account for 90% of invasive diseases. The protection against invasive pneumococci disease is related to the antibody specific to the capsular polysaccharide, the protection is therefore serotype specific.

It was surprisingly discovered that multivalent *S. pneumoniae* vaccines comprising of a PEG linker between the carrier protein and the polysaccharide to form two groups of compounds, wherein group one comprises monovalent bacterial capsular polysaccharide PEG compounds and the other group comprises bivalent and/or multivalent carrier protein compounds to provide substantially improved results. Specifically, the bivalent or multivalent compounds and bivalent uni-molecular compounds are preferably synthesized by the reaction between carrier protein and bifunctional PEG linkers attached to cross reactive *S. pneumoniae* serotypes. Results achieved are enormously improved compared to vaccines containing multivalent *S. pneumoniae* vaccine containing monovalent bacterial capsular polysaccharide coupled with the same number of serotypes with a direct conjugation between the two instead of a linker.

The present disclosure is directed to multivalent PEGylated compounds, of immunogenic compositions, and vaccines comprising carrier protein compounded to bacterial capsular polysaccharides using PEG linker and uses thereof.

The linker is used to PEGylate both polysaccharide as well as protein by connecting to PEG via two hydrazine functional groups cable of covalently compounding with both carrier protein as well as polysaccharides. This creates a new class of covalently compounded PEG products that have the additional effect of PEG on their properties compared to conjugates made by established methods. PEG has an additional enhancing effect on the immunogenicity of polysaccharides compared to regular conjugates and a depressing effect on the Immune response of carrier proteins. As the compounds of the invention contain polysaccharide coupled to PEG which is coupled to carrier, there is no conjugation between polysaccharide and protein.

This disclosure provides a universal method of covalent PEGylated compounds with a high immune response which is unaltered in spite of increase in serotypes. This unexpected beneficial observation is critically important in developing immunogenic compounds such as vaccines.

Protection against pneumococcal disease is obtained by antibodies produced against the polysaccharide component. By PEGylation, the response observed is twice that of PREVNAR®. This means that the high antibodies observed after administration of the PEGylated form of the vaccine will fall slowly, much more slowly that the rapid reductions observed with PREVNAR®. This is an entirely unexpected and extremely beneficial outcome. This result eliminates any need of a third injection saving cost as well as pain to infants and others caused by multiple injections, and in addition, makes protection more widely available, especially for those unable to return for repeated injections.

In particular, compositions of the invention comprise two or more bacterial capsular polysaccharides covalently connected to same protein to form PEGylated compounds, of various serotype antigens wherein the bacterial capsular polysaccharides and oligosaccharides are derived from serotypes of *Streptococcus pneumoniae*. The carrier protein is covalently connected to bacterial capsular polysaccharides through mono functional as well as bi-functional PEG linkers, preferably of defined lengths and the bi-functional linkers are, homo-bi-functional (subgroup Serotypes like 6A-6B or 19A-19F, and/or all other serotypes).

One embodiment of the invention is directed to multivalent covalently connected compound vaccines comprised of bivalent-polysaccharide protein compounds with enhanced immunogenicity. Bivalent compounds with general structure PS1-PEG-carrier protein-PEG-PS2 have higher immunogenicity compared to similar monovalent conjugates wherein PS1 and PS2 are two different serotype polysaccharides from gram-negative and gram-positive bacterial pathogens. By developing a bi-valent covalently compounded vaccine, the efficacy of the vaccine increases and carrier immunogenicity is reduced. The chemistry disclosed herein substantially increases immunogenicity, at the same time reduces carrier protein load.

Another embodiment of the invention is directed to vaccines with lower molecular weight polysaccharides and longer arm bifunctional linkers preferably with enhanced immunogenicity. Another embodiment of the invention is directed to providing higher immunogenicity and avidity of bivalent compounds as well as lower carrier protein immunogenicity. Another embodiment of the invention is directed to reducing covalently compounded vaccine dose with higher immunogenicity.

As disclosed herein, four parameters have been introduced to minimize the disadvantages of conventional vaccines:

Polysaccharide size is preferably 10-50 KDa.
Cross-reactive polysaccharides concurrent covalent connection to carrier protein.
Two or more cross reactive serotypes are covalently compounded concurrently with carrier proteins.
A long hetero- or homo-bifunctional PEG spacer arm is preferably from 2-40 Å (but may be from 2-40 Å, 4-40 Å, 10-40 Å, 20-40 Å, 9-20 Å, 5-20 Å, 5-30 Å).

These four parameters taken together are profoundly effective to increase the polysaccharide/protein ratio in the covalent compound to reduce carrier protein load, and to provide several folds of increase in immunogenicity and avidity.

The present invention is directed to polysaccharide-protein PEG compounds with enhanced immunogenicity displaying significantly high antibody titers. The carrier protein is obtained from, for example, tetanus toxoid, diphtheria toxoid, CRM197, tetanus toxoid fragments (TTHc), *N. meningitidis* protein PorB, RSV virus proteins, *B. pertussis* proteins like pertussis toxoid (PT), adenylate cyclase toxin (ACT), 69 KDa protein and Human Papilloma viral protein antigens or its VLP form, Hepatitis B core antigen or its VLP form or derivatives of HBsAg, and other conventional carriers. Polysaccharide fragment is obtained from group of group of gram positive bacteria and gram-negative bacteria, preferably from immunochemically cross-reactive polysaccharides of *S. pneumoniae*. The present invention is also directed to a process of preparing the polysaccharide-protein covalent PEG compound in which carrier protein reacts with cleaved and depolymerized polysaccharide fragments of optimum chain length.

Immunogenic compositions of the present invention provide improved protection against *S. pneumoniae* serotypes not found in PREVNAR-13®, and SYNFLORIX-10®.

Bivalent compounds with cross-reactive polysaccharides of *S. pneumoniae* serotypes (6A/6B, 9V/9N, 15A/15B and 19A/19F and similar cross-reactive serotypes) with short chain molecular size (10-50 KDa) were used to prepare 16-26-valent pneumococcal CPS PEG covalent compound vaccine in the present study. Pneumococcus type 6A and 6B polysaccharide was used as the model cross-reactive CPSs. CRM197 was used as the carrier protein for its clinical acceptance.

Multivalent mono-compounds have also been prepared using shorter PS chain length (0-50 KDa), long spacer arm (9-40 Å) with homo or hetero-bifunctional PEG or non-PEG linker with carrier protein CRM197.

CPS was activated either by oxidation or by cyanylation chemistry and oxidized by sodium periodate and introduced with either—reactive aldehyde or isothiocyanate (—OCN) groups in CPS.

Two strategies (short and long linker, short and long CPSs) were used to introduce, respectively. Physicochemical and immunological characteristics of the bivalent covalent compound vaccines were then investigated independently or combining with multivalent compound formulation.

The following examples illustrate embodiments of the invention, but should not be viewed as limiting the scope of the invention.

EXAMPLES

Example 1 Polysaccharide Size Reduction, Activation and PEGylation Compounding Process for Multiple *S. pneumoniae* Serotypes—1, 2, 3, 4, 5, 6A, 6B, 7F, 8, 10A, 11A, 12F, 14, 15A, 15B, 17F, 18C, 19A, 19F, 20, 22F, 23F and 35B.

Figure 1B:
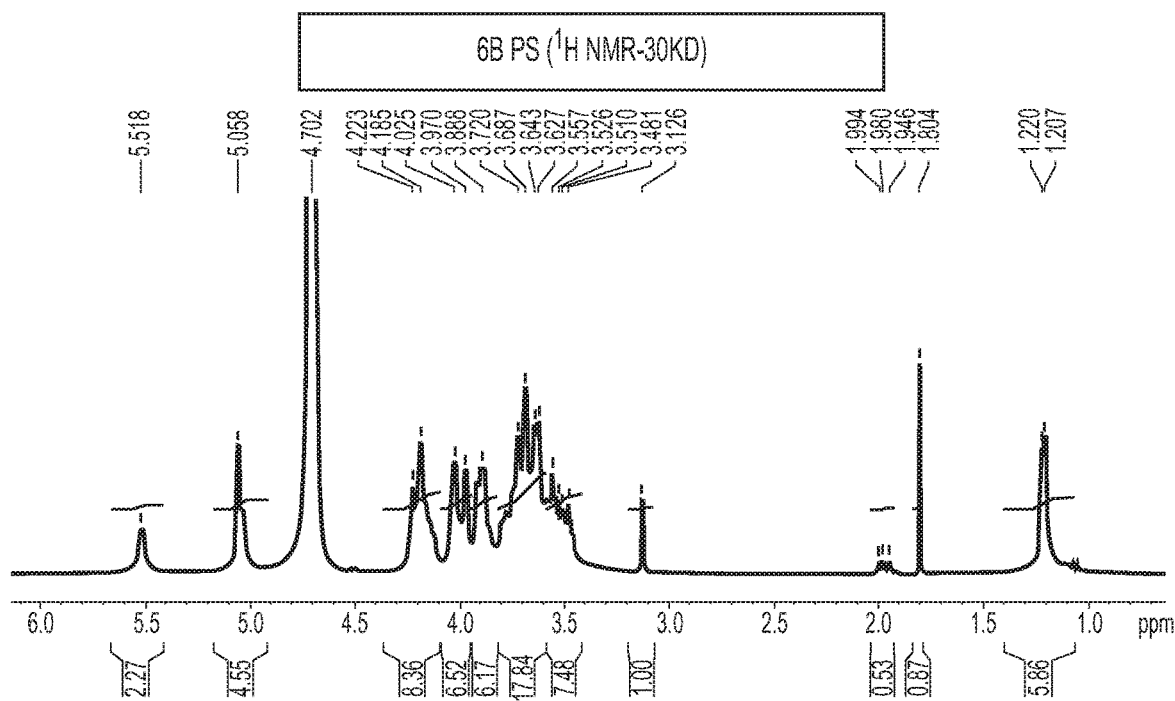
FIG. 1B Size reduced capsular polysaccharide of serotype 6B 1H-NMR spectra (500 MHz)-NMR data shows no loss of structural integrity compared to native PS.

6A and 6B Polysaccharide 100 mg each of capsular polysaccharides of *S. pneumoniae* 6A and 6B is dissolved in 10 ml of aqueous solution containing 10 mM of Acetic acid or 0.1 M HCl at pH 2.5-3.0 and hydrolysis is carried out by maintaining the solution at a temperature of 60-85° C. for a period of 60-120 mins. The so-obtained oligosaccharides after neutralization, diafiltered using 3-10 KDa TFF Centricon filters. Upon $^1$H NMR analysis (FIGS. 1A and 1B), the oligosaccharides formed show no loss of structural integrity or loss of epitope or repeat unit structure. Polysaccharides were measured using Anthrone assay and molecular size distributions (KDa) obtained are in the range of 10-50 KDa, 30-100 KDa, and 100-300 KDa.

CPS (50 mg) moiety (native polysaccharides of size between ≥200-500 KDa or size-reduced polysaccharides of size between 10-50 KDa) were activated cyanylation reagents commonly used in activation process (Table 1). Polysaccharide molecular size distributions were determined using SEC-HPLC (Shodex SB-405 and SB-406 SEC columns) with analysis using (10-1000 KDa) Pollulan mixture as reference standard (Pollulan standards from Shodex, USA).

Short spacer arm was introduced to PS by reaction with 5-8-fold molar excess of ADH (Sigma) at pH 5.6-6.0 for 3-5 hr. Long spacer arm (bifunctional linker or long 4-arm linker) was introduced into PS by reaction with 5-10-fold molar excess of at pH 5.6-6.0 for 3-5 h.

TABLE 1

Polysaccharide size distribution (KDa) used for conjugation

| PS | Polysaccharide KDa |
|---|---|
| 6A | 10-30 KDa |
| 6B | 20-50 KDa |
| 15B | 20-40 KDa |
| 18C | 20-50 KDa |
| 22F | 10-30 KDa |

Activated PS is further derivatized with short arm linker (adipic acid di-hydrazide, ADH, 174.2 g/mole), one more spacer arm linkers with varying size from 2-4 Å to 8-20 Å (600 g/mol-3.5 g/mole).

Homo-bifunctional PEG linkers with diamine functional groups attached, e.g. $NH_2$-PEG0.6K-$NH_2$, $NH_2$-PEG3.5K-COOH (Table 2).

TABLE 2

Short and long chain linker used for polysaccharide or carrier protein derivatization used (several other linkers either in pegylated form or non-pegylated form have also been used)

| Linker No. | Linker Structure | Chemical Structures/KDa or Å used |
|---|---|---|
| 1 | $NH_2$-PEG-$NH_2$/NHS | $H_2N—(CH_2CH_2O)_n—CH_2CH_2—NH_2$<br>1K and 3.5K |
| 2 | NHS/<br>$NH_2$-PEG-COOH | 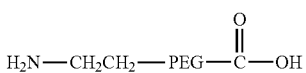<br>1K and 3.5K |
| 3 | Mal-PEG-$NH_2$ | 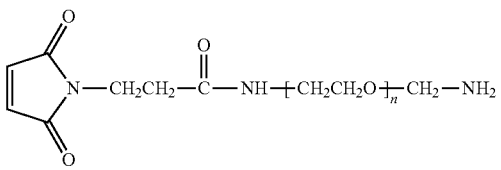<br>1K and 3.5K |

TABLE 2-continued

*Short and long chain linker used for polysaccharide or carrier protein derivatization used (several other linkers either in pegylated form or non-pegylated form have also been used)*

| Linker No. | Linker Structure | Chemical Structures/KDa or Å used |
|---|---|---|
| 4 | Mal-PEG-NHS | Structure: Maleimide—$CH_2CH_2$—PEG—C(=O)—O—NHS<br>1K and 3.5K |
| 5 | CHO-PEG-CHO | H—C(=O)—$CH_2CH_2$—O—$(CH_2CH_2O)_n$—$CH_2CH_2$C(=O)—H<br>1K and 3.5K |
| 6 | SH-PEG-$NH_2$ | HS—$(CH_2CH_2O)n$—$CH_2CH_2$—$NH_2$<br>1K and 3.5K |
| 7 | ADH | $H_2N$—NH—C(=O)—$(CH_2)_4$—C(=O)—NH—$NH_2$ |
| 8 | HZ-PEG-HZ | $H_2N$—NH—C(=O)—$CH_2$—O—$(CH_2CH_2O)_3$—$CH_2$—C(=O)—NH—$NH_2$<br>PEG |
| 9 | SMPH | NHS-ester—$(CH_2)_5$—NH—C(=O)—$(CH_2)_2$—Maleimide<br>SMPH<br>Succicidinyl [6-(5-oxobisbutyl-amido-hexanote]<br>MW 378.35<br>Spacer Arm 14.2 Å |
| 11 | SMCC | NHS-ester—cyclohexane—$CH_2$—Maleimide<br>SMCC<br>Succicidinyl 4-(6-nucleodimethyl)cyclohexane-1-carboxylate<br>MW 284.93<br>Spacer Arm 8.2 Å |

TABLE 2-continued

Short and long chain linker used for polysaccharide or carrier protein derivatization used (several other linkers either in pegylated form or non-pegylated form have also been used)

| Linker No. | Linker Structure | Chemical Structures/KDa or Å used |
|---|---|---|
| 12 | 4-Arm-PEG-NH$_2$ or NHS | 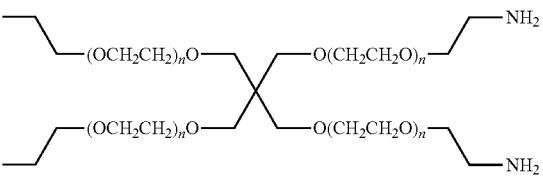 |

Mal-Maleimide,
NHS-Succinimide,
PEG-Polyethylene glyscol derivatives,
ADS-Adipic acid di-hydrazide.

Two aliquots of 2 ml each of the derivatized CPS (10 mg/ml) were mixed with 1 ml aliquot of the two CRM197 protein samples (10 mg/ml) at 4° C. for 8-12 hrs. The compounds with long and short spacer arm were purified by a 100-300 KDa Centricon filters (EMD Millipore) (Table 3).

TABLE 3

Physicochemical Characterization of mono-valent Compounds

| PS | Activated PS KDa by SEC-HPLC | Compounds KDa by SEC-HPLC | PS:Protein ratio | Free PS % |
|---|---|---|---|---|
| 6A | 10-30 KDa, 200-300 KDa | >200-300, >2500 | 0.5-2, 1-2 | <2 |
| 6B | 20-50 KDa, 200-400 KDa | >300-500, >2500 | 0.5-2, 1-2 | <1 |
| 15B | 20-40 KDa | >300-500 | 0.5-2, 1:1 | <1 |
| 18C | 20-50 KDa | >300-500 | 0.5-2, 1:1 | <2 |
| 22F | 10-30 KDa | >200-300 | 0.5-2, 1:1 | <1 |

Note:
Internal std. for KDa determination of PS for SEC-HPLC:Pullulan std. mixture (2 KDa-2500 KDa).

Figure 5:
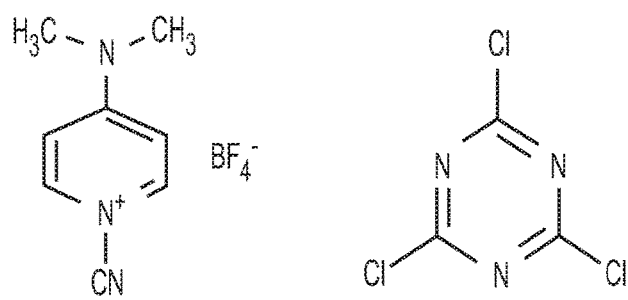
FIG. 5 CDAP (1-cyano-4-dimethylaminopyridinium tetrafluoroborate, Cyanuric chloride (2,4,6-Trichloro-1,3,5-triazine), cyanogen bromide (CNBr).
Figure 6:
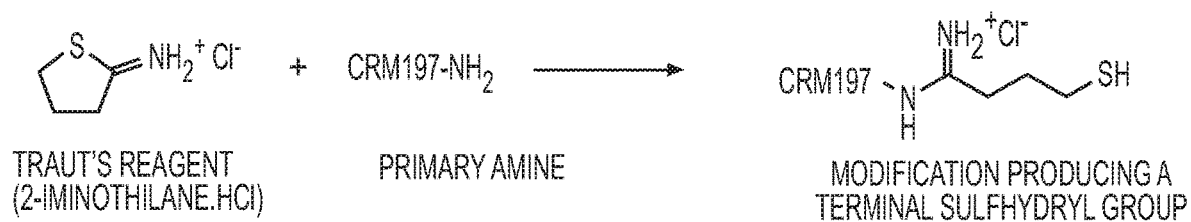
FIG. 6 Thiolation of CRM197 with iminotiolene.

Example 2 Activation of Size Reduced Polysaccharides of Different Molecular Weights Oligosaccharides of Different Molecular Weights Synthesized as Described in Example 1 were Activated Cyanylation Reagents Commonly used in Activation Process CDAP (1-Cyano-4-diethylaminopyridinium tetrafluoroborate (Sigma Aldrich, USA)) cyanuric chloride (2,4,6-trichloro-1,3,5-triazine) or cyanogen bromide (CNBr) and coupling carrier protein (see FIGS. 5 and 6).

Polysaccharide solution (10 mg/ml) was incubated with 10 mg/ml CDAP (100 mg/ml in acetonitrile) in 2M NaCl or 200-300 mM bicarbonate buffer at RT for 4-6 minutes. pH was maintained at 10-10.5 using either 1N NaOH or 1N HCl. Then, pH was adjusted to 8.1-8.2, pegylated linkers (Hz-PEG-HZ) were allowed to react with CDAP treated PS. For 8-12 hrs at RT. The reaction mixtures were depth filtered followed by 100-300 KDa cutoff centricon filters 5-8 times using 150 mM NaCl.

Derivatization of Activated Size Reduced Polysaccharides

Activated oligosaccharides were further derivatized with short chain homo-bifunctional PEG hydrazide linker. Typical reagent was adipic Acid di-hydrazide, ADH, Molecular weight 174.2 g/mole). Homo or hetero-bifunctional PEG linkers bearing di-amine, di-hydrazide, or amine or hydrazide-carboxylic acid/aldehyde functional groups, e.g. NH2-PEG(1K-3.5K)-NH2, HZ-PEG(1-3.5K)-HZ, NH2-PEG3.5K-COOH were used. (Table 2). Several other homo- or hetero-bifunctional spacer arms can also be used for derivatization (Table 2). Short spacer arm was introduced to oligosaccharide by reaction with 5-8 fold molar excess of adipic acid di-hydrazide (Sigma) at pH 5.8-6.0 for 3-5 hr. long chain PEG linker (bifunctional linker or long tetra functional linker (Table 2), No. 12 four arm PEG linker) was introduced into Polysaccharide by reaction with 5-10-fold molar excess of the linker to the oligosaccharide at pH 5.8-6.0 for 3-5 hrs. at RT.

Derivatization of Carrier Protein with Short or Long-Linkers

Carrier protein CRM197 was further derivatized with short chain homo-bifunctional PEG hydrazide linker. Typical reagent was adipic Acid di-hydrazide, ADH, molecular weight 174.2 g/mole). Homo or hetero-bifunctional PEG linkers bearing di-amine, di-hydrazide, or amine or hydrazide-carboxylic acid/aldehyde functional groups, e.g., NH2-PEG(1K-3.5K)-NH2, HZ-PEG(1-3.5K)-HZ, NH2-PEG3.5K-COOH were used. (Table 2). Several other homo- or hetero-bifunctional spacer arms can also be used for derivatization as listed in Table 2). Short spacer arm was introduced to carrier protein CRM197 by reaction with 5-8 fold molar excess of adipic Acid di-hydrazide (Sigma) at pH 5.8-6.2 in 300-600 mM MES buffer for 3-5 hr at RT. Long chain PEG linker (bifunctional linker or long tetra functional linker (Table 2, No. 12 four arm PEG linker) was introduced into carrier protein by reaction with 5-10-fold molar excess of the linker to the oligosaccharide at pH 5.8-6.2 in 300-600 mM MES buffer for 3-5 hr at RT (room temperature).

Example 3 Cross-Reactive Polysaccharide Serotypes Activation and Attachment of Short or Long-PEG Spacer Arm Linkers (Serotypes of Interest are 6A/6B, 9V/9N, 15A/15B and 19A/19F or any Other Cross-Reactive Serotypes)

Activation of the oligosaccharide derived from the capsular polysaccharide of S. pneumoniae Type 6A and 6B covalently compounding with CRM197 and introduction of the primary amino groups to the oligosaccharides concurrently.

Native or size reduced polysaccharide of serotype 6A and 6B (≥200-400 KDa) were covalently compounded using the same procedure as described in Examples 1 and 2.

The oligosaccharides mixture thus obtained as reported in Example 1 are dissolved in WFI, to an end concentration of 10 mg/ml. At the end of the reaction, the Oligosaccharide are purified by diafiltration using 3-10 KDa Centricon filters.

The Oligosaccharides into which the amino groups have been introduced are diluted to a concentration of 10 mg/ml in an aqueous solution of DMSO (at 20-30% v/v) to DMSO containing ADH short PEG linker or long spacer arm PEG linkers in molar excess relatively to the amino groups introduced into the oligosaccharide (usually 5-10:1). The reaction was carried out by keeping the solutions at RT for a time of 4-12 hours. At the end of the period, oligosaccharide was again purified using 3-10 KDa Centricon filters.

Example 4 Synthesis of Pneumococcal Polysaccharide Monovalent PEG Compounds

Two separate aliquots of same or differently size reduced and derivatized size reduced Polysaccharides (with short PEG spacer arm ADH and Long. PEG spacer arm HZ-PEG-HZ) as synthesized in example 3 (10 mg/ml) were mixed with 1 ml aliquot of the CRM197 protein sample (10 mg/ml) at 4° C. for 8-12 hrs. The compounds containing both long and short chain linkers were purified using 100-300 KDa Centricon filters (EMD Millipore). Monovalent compounds were assayed for total polysaccharide content by either anthrone or uronic acid assay, total protein content by BCA or Lowry assay (Table 4).

All other cross-reactive Polysaccharide covalent compounds are made using the same procedure as above.

TABLE 4

Physicochemical Characterization of Bi-valent Compounds of general structure 6A-CRM197-6B

| PS | Activated Oligosaccharide KDa | Covalent. compound KDa | Oligosaccharide:Protein ratio (Weight ratio) | Free Oligosaccharide % by weight |
|---|---|---|---|---|
| 6A | ≥100-300 KDa | >200-300 KDa, >2500 KDa | 0.5-2, 1-2 | <2 |
| 6B | ≥200-400 KDa | >300-500 KDa, >2500 KDa | 0.5-2, 1-2 | <1 |
| 6C | ≥200-400 KDa | >300-500 KDa, >2500 KDa | 0.5-2, 1-2 | <1 |
| 15B | ≥100-300 KDa | >300-500 KDa, >1500 KDa | 0.5-2, 1:1 | <1 |
| 15A | ≥100-300 KDa | >300-500 KDa, >1500 KDa | 0.5-2, 1:1 | <1 |
| 18C | ≥100-300 KDa | >300-500 KDa, >1500 KDa | 0.5-2, 1:1 | <2 |
| 22F | ≥100-300 KDa | >200-300 KDa, >1000 KDa | 0.5-2, 1:1 | <1 |
| 1 | ≥100-300 KDa | >200-300 KDa, >2500 KDa | 0.5-2, 1-2 | <2 |
| 3 | ≥200-400 KDa | >300-500 KDa, >2500 KDa | 0.5-2, 1-2 | <1 |
| 4 | ≥100-300 KDa | >300-500 KDa, >1500 KDa | 0.5-2, 1:1 | <1 |
| 7F | ≥100-300 KDa | >300-500 KDa, >1500 KDa | 0.5-2, 1:1 | <2 |
| 9V | ≥100-300 KDa | >200-300 KDa, >1000 KDa | 0.5-2, 1:1 | <1 |
| 9N | ≥100-300 KDa | >200-300 KDa, >1000 KDa | 0.5-2, 1:1 | <1 |
| 14 | ≥100-300 KDa | >200-300 KDa, >2500 KDa | 0.5-2, 1-2 | <2 |
| 18C | ≥200-400 KDa | >800 KDa, >2500 KDa | 0.5-2, 1-2 | <1 |
| 19A | ≥100-300 KDa | >300-500 KDa, >1500 KDa | 0.5-2, 1:1 | <1 |
| 19F | ≥100-300 KDa | >300-500 KDa, >1500 KDa | 0.5-2, 1:1 | <2 |
| 23F | ≥100-300 KDa | >200-300 KDa, >1000 KDa | 0.5-2, 1:1 | <1 |
| 33F | ≥100-300 KDa | >200-300 KDa, >2500 KDa | 0.5-2, 1-2 | <2 |

Note:
Internal std. for SEC-HPLC (KDa):Pollulan std mixture (2 KDa-1200 KDa)

Example 4 Investigational Formulation of 16V-Or higher Valent Pneumococcal Covalent Compound Vaccine Pneumo polysaccharide-CRM197 covalent compounds for serotypes containing 1, 3, 5, 7F, 14, 15B, 18C, 22F, 23F, 33F, 35B and cross-reactive polysaccharide compounds 6A, 6B, 9V, 9N, 15A, 15B, 19A, and 19F were combined to yield final antigen concentration of 4.0 µPS/mL. Sodium chloride (150 mM) solution, 10-20 mM Histidine, succinic acid and 0.001% Tween-20 was also used during the formulation process as diluent, and aluminum phosphate (Adju-Phos, Brenntag, USA) was used as investigational adjuvant. 16-V compound was aseptically filled in 2 mL sterile vials. PNEUMOVAX® (Merck, USA) or PREVNAR-13® (Pfizer, USA) was used as two control commercial vaccine formulation.

Example 5 Immunogenicity Studies of Covalent Compounds

Figure 2A:
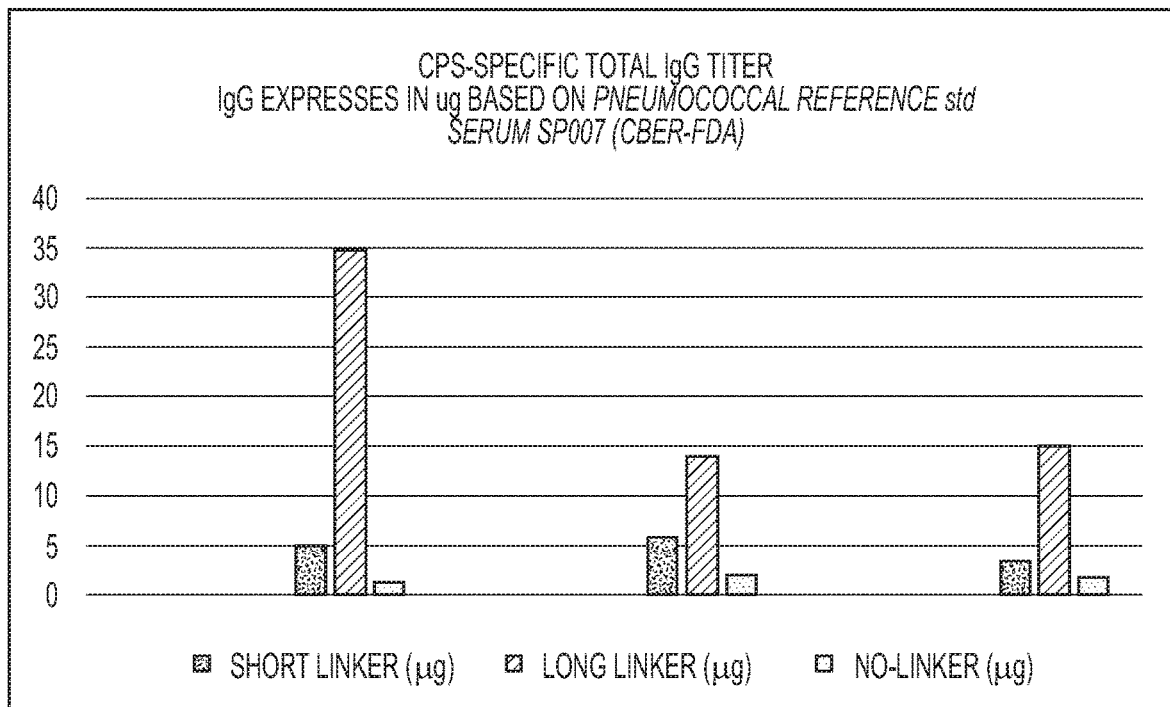
FIG. 2A Capsular polysaccharide specific antibodies (total IgG) using multiplex bead based assay procedure (Polysaccharides used for these compounds are in the range of 10-50 KDa).
Figure 2B:
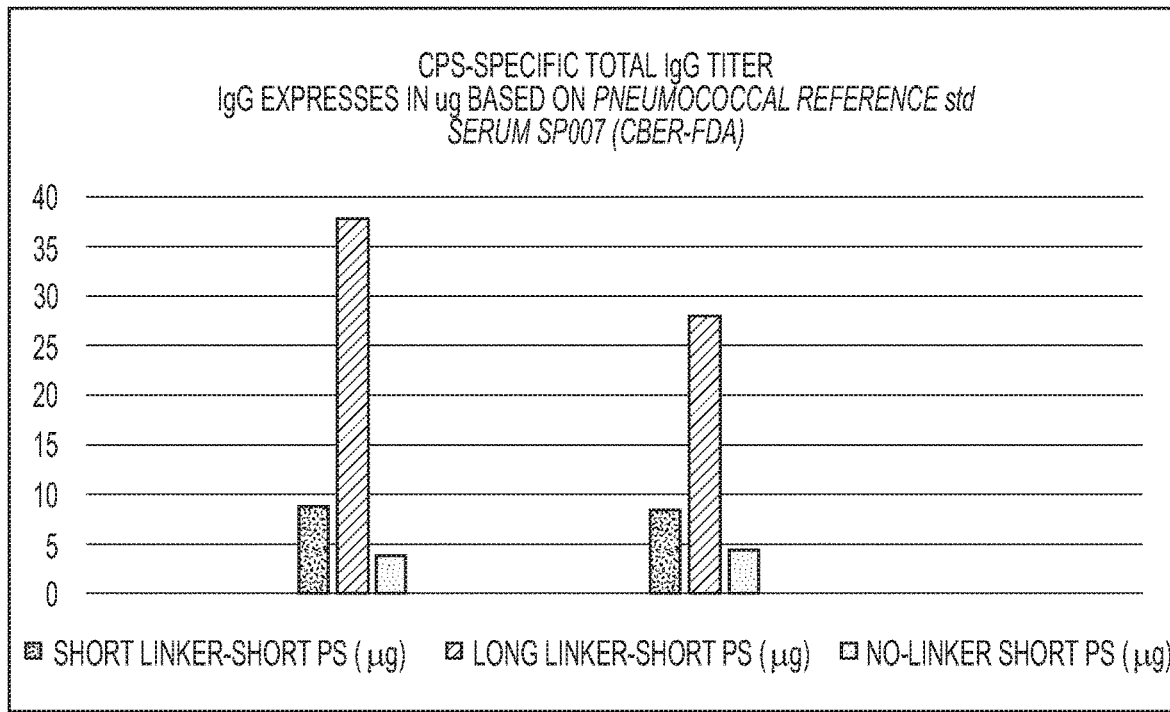
FIG. 2B Capsular polysaccharide specific antibodies (total IgG) using multiplex bead based assay procedure wherein polysaccharides are in the range of 200-300 KDa or more.
Figure 2C:
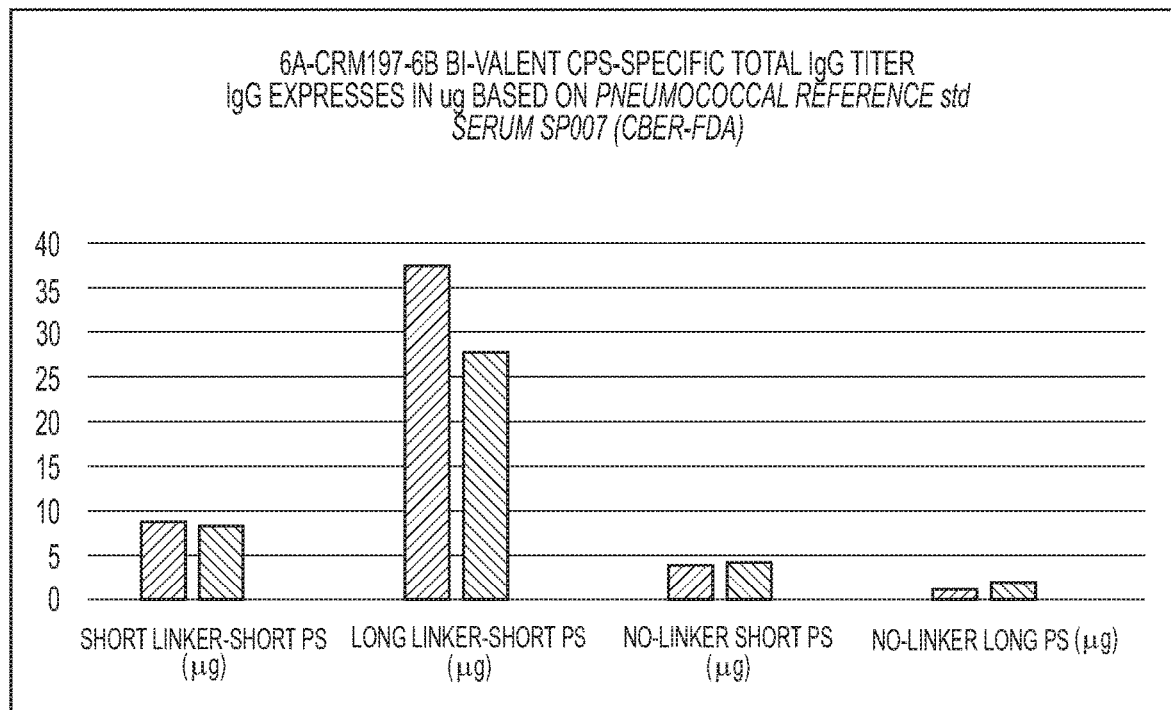
FIG. 2C Bi-valent compounds of 6A and 6B capsular polysaccharide specific antibodies (total IgG) using multiplex bead based assay procedure wherein polysaccharides are in the range of 10-50 KDa and 200-400 KDa.
Figure 3A:
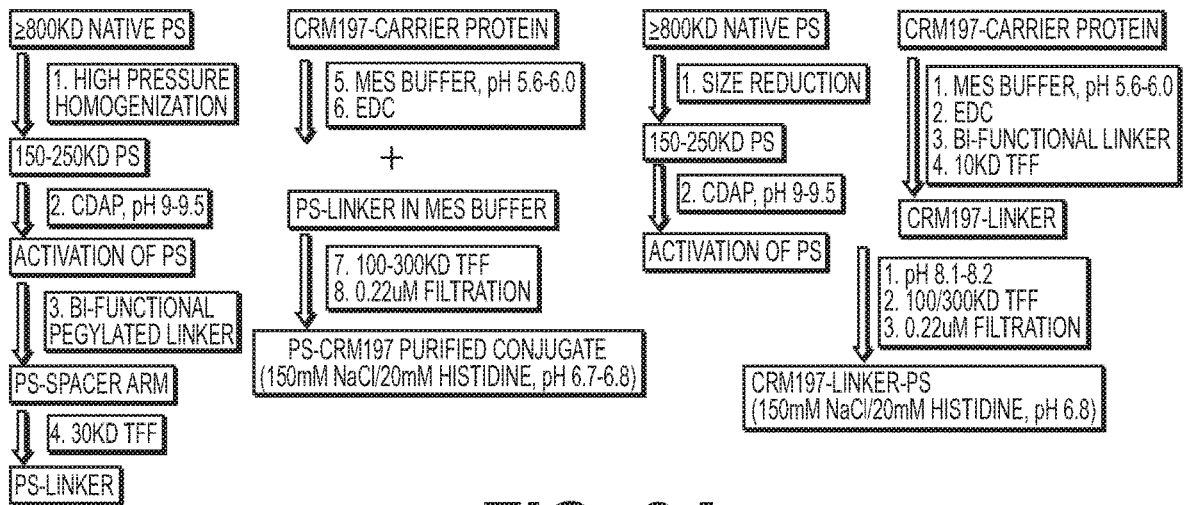
FIG. 3A Monovalent compounds synthesis work flow chart.
Figure 3B:
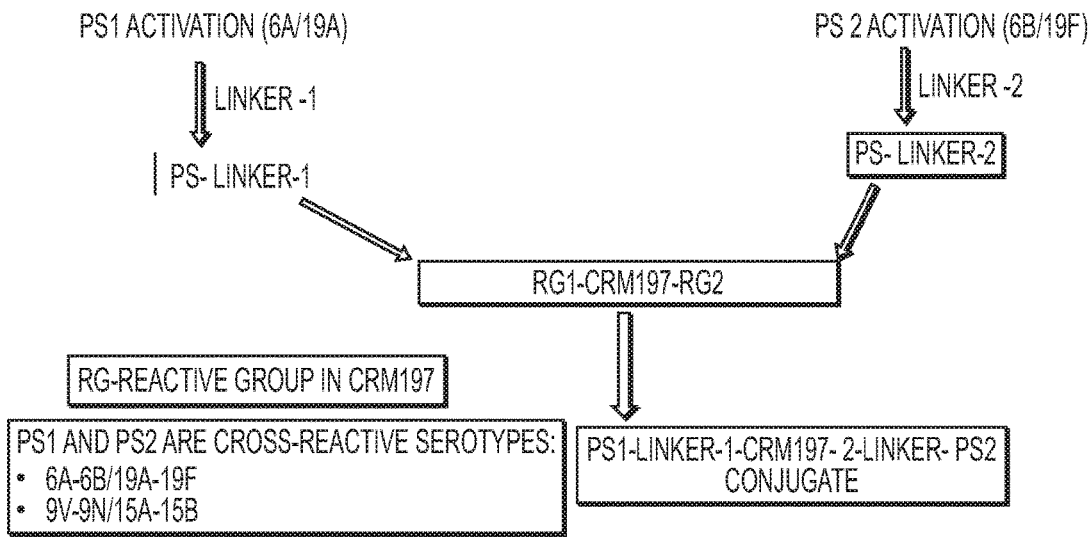
FIG. 3B Flow chart of PS1 and PS2 activation with linkers.
Figure 4A:
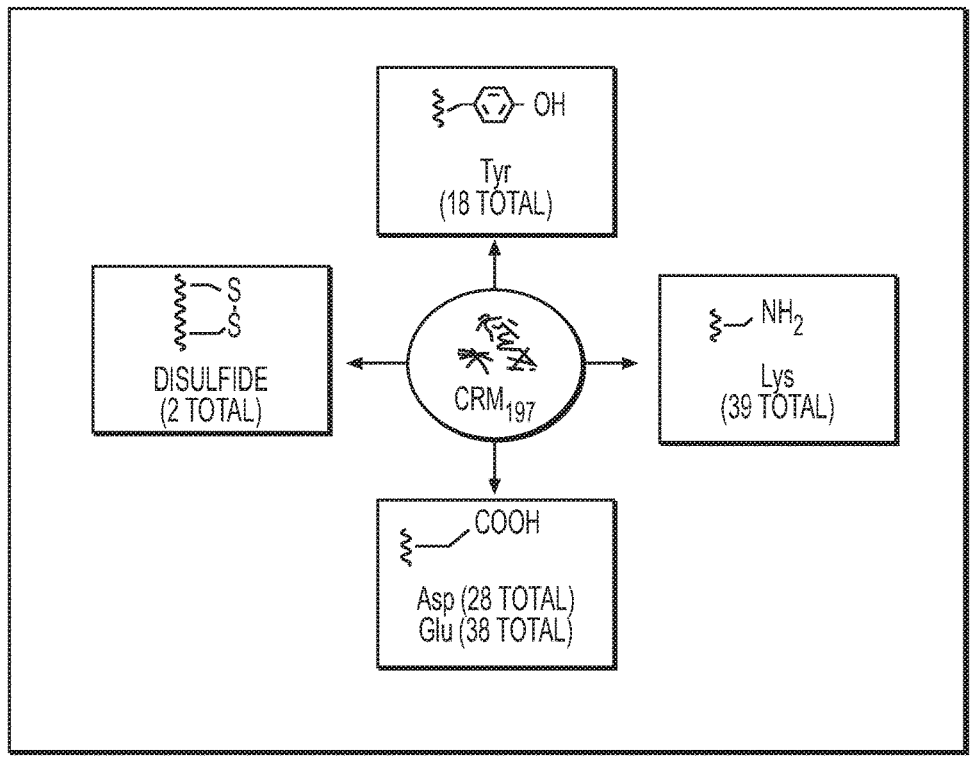
FIG. 4A Bivalent unimolecular compounds and bi-valent compounds synthesis workflow chart.
Figure 4B:
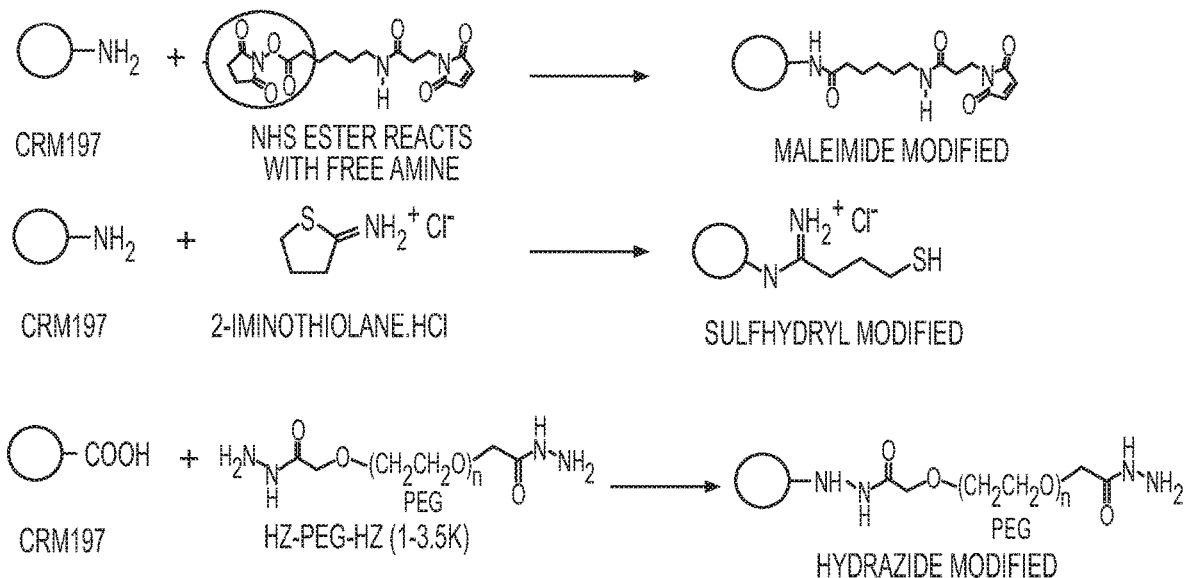
FIG. 4B CRM chemical couplings.

A New Zealand white rabbit model (NZW) was selected in this work to compare the immunogenicity of the Pneumo PS-CRM197 covalent compounds. Rabbits from all groups (16-V {valent}, PREVNAR-13®, and PNEUMOVAX®) were examined for clinical signs before and after immunization periods. For all groups, pre-immunization, booster dose (7 and 14-days) and terminal bleed (28 days) were collected and aliquoted and store at minus 80° C. until use. Multiplexed Immunogenicity assay for the determination of Total IgG were performed according to the standard protocol using reference standard serum 007 (CBER, FDA, USA). Reference serum and rabbit serum were diluted and pre-adsorbed for cross-reacting antibodies by treatment with pneumococcal CWPS and either 22F PS or 25PS. Human monoclonal anti-polysaccharide antibodies (Pamlico Biopharma, USA) were used for total IgG estimation. Bio-Plex 200 (Bio-Rad). Multiplex reader was used as per manufacturer's instructions (see FIGS. 2A, 2B and 2C).

Example 5 S. pneumoniae Cross-Reactive Capsular Polysaccharide Serotypes Activation and Attachment of Short and Long-Spacer Linkers Serotypes of 6A/6B, 9V/9N, 15A/15B and 19A/19F which are cross-reactive serotypes are used for the synthesis of bi-valent covalent compounds containing capsular poly saccharides and carrier protein. Bivalent covalent compounds by definition contain two capsular polysaccharide attached to CRM 197 simultaneously or concurrently.

Activation of the size reduced polysaccharide derived from the capsular polysaccharide of S. pneumoniae Type 6A and 6B, covalently compounded with CRM197 and introduction of the primary amino or hydrazide groups to the oligosaccharides carried out concurrently.

Native polysaccharides or size reduced oligosaccharide of serotype 6A and 6B (≥200-500 KDa) were covalent compounded using the same procedure as described in Example 1-4.

The size reduced polysaccharides mixtures thus obtained were dissolved in water for injection, so that the final concentration was 10 mg/ml. The size reduced polysaccharides into which the amino or hydrazide groups were introduced were diluted to a concentration of 10 mg/ml in an aqueous solution of dimethyl sulfoxide (DMSO) so the percentage of DMSO was in the range of 20-30% (v/v). This was added to DMSO containing short chain linker such as ADH or long chain linkers as described in Table 2 in molar excess relatively to the amino/hydrazide groups introduced into the size reduced polysaccharides (usually 5:1 or 10:1), more specifically 8:1.

The reaction was carried out at room temperature for a duration of 4-12 hours. At the end of the reaction period, the reaction product was again purified using 3-10 KDa Centricon filters.

Example 6 Simultaneous or Concurrent Covalent Compounds of S. pneumoniae Oligosaccharides of Type 6A and Type 6B with CRM197 Carrier Protein as Bivalent Compound Manufacturing The aqueous solution containing 15 mg/ml of CRM197, was added to DMSO containing the linker attached oligosaccharide (20-30% in water) derived from the capsular polysaccharide of S. pneumoniae Type 6A. The ratio of PEG linker attached oligosaccharide to CRM197 was selected from 1:1.2:1.1:2. The mixture so obtained was kept, under mild stirring, at room temperature for 8-12 hrs. At the end of said time, the solution containing the derivatized oligosaccharide derived from the capsular polysaccharide of S. pneumoniae 6B was added. The molar ratio of capsular polysaccharide of S. pneumoniae 6B to the CRM197, was selected from 1:1.2:1.1:2). The resulting mixture was kept for 8-12 hrs at room temperature (Table 5). The covalent compounding reaction can also be carried out by adding, at the same time (concurrently), to the CRM197-containing solution, the two-activated oligosaccharide respectively derived from the capsular polysaccharide of S. pneumoniae Type 6A and from the capsular polysaccharide of S. pneumoniae Type 6B. The oligosaccharide-protein covalent compounds so obtained were dialyzed using 100-300 KDa dialysis membrane (Spectrum lab, USA), conditioned in 0.01 M phosphate buffer containing 0.2M NaCl (pH=6.6-7.0) and finally filtered through a 0.22 μm filter.

All other cross-reactive polysaccharide compounds were made using the same procedure as used above. Reaction sequences are depicted in FIGS. 3A, 3B, 4A, and 4B.

TABLE 5

Comparisons of PS Contents

| Bivalent Oligosaccharide | Activated oligosaccharide KDa | Covalent compounds KDa | Total Polysaccharide Protein ratio by weight | Free oligosaccharide % by weight |
|---|---|---|---|---|
| 6A-6B | ≥100-300 | 2.0:1.5 | 2-1.5 (1:0.75) | <2 |
| 6A-6B | ≥100-300, ≥300 | >1200-2500 KDa | 2-1.4 (1:0.7) | <3 |
| 19A-19F | ≥100-300 | >500-800 KDa | 2-1.6 (1:0.8) | <2 |
| 15A-15B | ≥100-300, ≥300 | >500-1000 KDa | 2-1.3 (1:0.65) | <3 |
| 9V-9N | ≥100-300, ≥300 | >500-1000 KDa | 2-1.3 (1:0.65) | <3 |

Example 7 Investigational Formulation of 18-Valent or Higher Valent Pneumococcal Covalent Compound Vaccine Pneumococcal polysaccharide-CRM197 covalent. Compounds for serotypes containing 1, 3, 5, 7F, 14, 18C, 22F, 23F, 33F, 35B (10 serotypes polysaccharides) and cross-reactive polysaccharide compounds of (6A, 6B), (9V, 9N), (15A, 15B) and (19A, 19F) (8 serotypes) were combined to yield final polysaccharide concentration of 2.2-4.4 μg PS/mL (1.1-2.2 μg/human dose, 0.5 mL). Sodium chloride (150 mM) solution, 10-20 mM histidine, 20 mM HEPES or MOPS buffer and 0.001% Tween-20 was also used during the formulation process as diluent, and aluminum phosphate (Adju-Phos, Brenntag, USA) was used as investigational adjuvant.

18-valent or higher valent (>20V-24V) covalent compound was aseptically filled in 2 mL sterile vials. PNEUMOVAX® (Merck, USA) and/or PREVNAR-13® (Pfizer, USA) were used as controls.

Example 9 Immunogenicity Studies of the Covalent Compounds

A New Zealand white rabbit model (NZW) was selected in this work to compare the immunogenicity of the Pneumococcal PS-CRM197 covalent compounds. Rabbits from all groups (18 or higher-valent compounds, PREVNAR-13®, Pfizer and PNEUMOVAX®-23 (Merck USA) were examined for serological titers before and after immunization periods. For all groups, pre-immunization, booster dose (7 and 14-days) and terminal bleed (28 days) were collected and aliquoted and store at minus 80° C. until use. Immunogenicity assay for the determination of Total IgG were performed according to the standard protocol using reference standard serum 007 (CBER, FDA, USA). Reference serum and Rabbit serum were diluted and pre-adsorbed for cross-reacting antibodies by treatment with Pneumococcal CWPS and non-vaccine serotype 25PS. Human/rabbit/mouse monoclonal anti-polysaccharide antibodies were used for total IgG estimation. Bio-Plex 200 (Bio-Rad) reader were used as per the manufacturer's instructions.

Immunogenicity of the compounds, i.e. capsular polysaccharide specific antibodies (total IgG) were measured using bead-based ELISA assay method were given in Table 6. Total IgG values were compared head to head with PREVNAR-13® in rabbit immunogenicity data. 14-day data shows significant increase in titer in IVT-18V-1 vaccine compared to PREVNAR-13® vaccine. Similarly, IVT-18V-1 data has significant booster on IgG values as compared to PREVNAR-13® (Table 6).

TABLE 6

Capsular Polysaccharides specific antibodies (Total IgG in µg/ml) using Multiplex bead-based ELISA assay for 18V-monovalent covalent compound vaccines

| PREVNAR-® 13® 2.2 µg/dose | (IgG) 14 day/ zero day | (IgG) 28 day/ Zero day | IVT-18V- 1 2.2 µg/dose | (IgG) 14 day/ Zero day | (IgG) 28 day/ Zero day |
|---|---|---|---|---|---|
| 1 | 45 | 350 | 1 | 375 | 1500 |
| 3 | 47 | 200 | 3 | 48 | 480 |
| 6A | 188 | 560 | 6A | 775 | 3775 |
| 6B | 165 | 780 | 6B | 662 | 3662 |
| 18C | 50 | 280 | 18C | 306 | 3560 |
| 19A | 45 | 235 | 19A | 233 | 2500 |
| 19F | 29 | 290 | 19F | 72 | 720 |
| 4 | 49 | 230 | 4 | 150 | 750 |
| 5 | 186 | 700 | 5 | 550 | 3550 |
| 7F | 180 | 680 | 7F | 332 | 3860 |
| 9V | 52 | 520 | 9V | 212 | 2400 |
| 9N | — | — | 9N | 200 | 2200 |
| 14 | 85 | 400 | 14 | 272 | 2890 |
| 15A | — | — | 15A | 672 | 3900 |
| 15B | — | — | 15B | 750 | 4000 |
| 18C | 175 | 800 | 18C | 550 | 5500 |
| 22F | — | — | 22F | 1000 | 8000 |
| 23F | 53 | 450 | 23F | 212 | 2420 |

Note:
IVT-18V = 18-V compound vaccine (monovalent covalent PEG compounds mixed together); 9N, 15A, 15B, 22F and 23F serotype are not present in PREVNAR-13 ®, so IgG values not measured; 18-V formulation as monovalent covalent compounds were prepared using 2.2 µg for each serotype except 4.4 µg of 6B covalent PEG compounds. Sodium chloride (150 mM) solution, 10-20 mM histidine, 20 mM HEPES or MOPS buffer and 0.001% Tween-20 was also used during the formulation process as diluent, and aluminum phosphate (Adju-Phos, Brenntag, USA) was used as investigational adjuvant; capsular polysaccharides antibodies (total IgG) using bead-based ELISA: 18-V covalent PEG compounds vaccine formulation-2 (IVT-18V-2): 10-V formulation as monovalent covalent compounds and remaining 8-V added as bivalent-covalent PEG compounds which includes 6A/6B, 9V/9N, 15A/15B and 19A/19F. (vaccine dose used as 2.2 µg for each serotype except 4.4 µg of 6B) 10-V formulation as monovalent compounds and remaining 8-V added as bivalent-compounds which includes 6A/6B, 9V/9N, 15A/15B and 19A/19F. 6A-6B bivalent unimolecular compounds are used as 2.2 µg/dose, remaining bivalent compounds are used as 2.2 µg/dose. Sodium chloride (150 mM) solution, 10-20 mM histidine, 20 mM HEPES or MOPS buffer and 0.001% Tween-20 was also used during the formulation process as diluent, and aluminum phosphate (Adju-Phos, Brenntag, USA) was used as investigational adjuvant.

Immunogenicity of the covalent PEG compounds, capsular polysaccharide specific antibodies (total IgG) were measured using bead-based ELISA assay method were given in Table 7. Total IgG values were compared head to head with PREVNAR-13® in rabbit immunogenicity data. 14-day data shows significant increase in titer in IVT-18V-2 vaccine compared to PREVNAR-13® vaccine. Interestingly, IVT-18V-2 total IgG data for bivalent compounds serotypes (for example. 6A/6B, 9V/9N, 15A/15B, and 19A/19F) has significant booster on IgG values as compared to IVT-18V-1 formulation with monovalent covalent PEG compounds. Therefore, it can be concluded that Bivalent covalent PEG compounds have better immunogenicity in comparison to monovalent covalent PEG compounds (Table 7). Therefore, IVT-18V-2 covalent PEG compounds vaccine formulation has superior immunogenicity not only against PREVNAR-13® but also against IVT-18V-1 formulation. Polysaccharide covalent PEG compounds with either 1-3.5K linker (HZ-PEG-HZ) elicits much higher immunogenicity in compared to short linker (ADH) or no linker conjugates as in PREVNAR-13®.

TABLE 7

Capsular Polysaccharides antibodies (total IgG) using Multiplex bead-based ELISA

| PREVNAR- 13 ® 2.2 µg/dose | Ratio 14 day/ 0 day | Ratio 28 day/ 0 day | IVT-18V- 2 2.2 µg/dose | Ratio 14 day/ 0 day | Ratio 28 day/ 0 day |
|---|---|---|---|---|---|
| 1 | 45 | 350 | 1 | 375 | 1500 |
| 3 | 47 | 200 | 3 | 50 | 530 |
| 6A | 188 | 560 | 6A/6B | 875/762 | 4375/4662 |
| 6B | 165 | 780 | | | |
| 18C | 50 | 280 | 18C | 316 | 3600 |
| 19A | 45 | 235 | 19A/19F | 300/198 | 3500/2700 |
| 19F | 29 | 290 | | | |
| 4 | 49 | 230 | 4 | 180 | 1000 |
| 5 | 186 | 700 | 5 | 550 | 3600 |
| 7F | 180 | 680 | 7F | 360 | 4100 |
| 9V | 52 | 520 | 9V/9N | 350/300 | 3400/3200 |
| 9N | — | — | | | |
| 14 | 85 | 400 | 14 | 310 | 32000 |
| 15A | — | — | 15A/15B | 872/850 | 5900/5600 |
| 15B | — | — | | | |
| 18C | 175 | 800 | 18C | 600 | 6800 |
| 22F | — | — | 22F | 1020 | 8150 |
| 23F | 53 | 450 | 23F | 300 | 3200 |

Note:
IVI-18V-2 = 10-monovalent compounds and 4 bivalent compounds mixed together; 18-V compound vaccine formulation (IVT-18V-3): 10-V formulation as monovalent compounds used as 2.2 µg/dose and remaining 8-V added as bivalent-compounds which includes 6A/6B, 9V/9N, 15A/15B and 19A/19F used as 1.1 µg/dose, except 6B 2.2 µg/dose.

Immunogenicity of the compounds, i.e. capsular polysaccharide specific antibodies (total IgG) were measured using multiplex bead-based ELISA assay method were given in Table 8. Total IgG values were compared head to head with PREVNAR-13® in rabbit immunogenicity data. 14-day data shows significant increase in titer in IVT-18V-3 vaccine compared to PREVNAR-13® vaccine. Interestingly, IVT-18V-3 formulations with lower dose (2.2 vs 1.1 ug dose), total IgG data for bivalent compounds serotypes (for example. 6A/6B, 9V/9N, 15A/15B, and 19A/19F) has comparable IgG values as compared to IVT-18V-2 formulations for bivalent compound serotypes. Therefore, it can be concluded that bivalent compounds have better immunogenicity in comparison to monovalent compounds with lower dose. Therefore, IVT-18V-2 compound vaccine formulation has superior immunogenicity not only against PREVNAR-13® but also against IVT-18V-1 formulation. Polysaccharide compounds with either 1-3.5K linker (HZ-PEG-HZ) elicits much higher immunogenicity in compared to short linker (ADH) or no linker conjugates as in PREVNAR-13® (Table 8).

TABLE 8

Total IgG data for bivalent compounds serotypes

| PREVNAR®-13® 2.2 µg/dose | Ratio 14 day/0 day | Ratio 28 day/0 day | IVT-18V-2 2.2 µg/dose | Ratio 14 day/0 | Ratio 28 day/0 day |
|---|---|---|---|---|---|
| 1 | 45 | 350 | 1 | 375 | 1500 |
| 3 | 47 | 200 | 3 | 50 | 530 |
| 6A | 188 | 560 | 6A/6B | 825/860 | 4275/4900 |
| 6B | 165 | 780 | | | |
| 18C | 50 | 280 | 18C | 316 | 3600 |
| 19A | 45 | 235 | 19A/19F | 275/250 | 3400/3000 |
| 19F | 29 | 290 | | | |
| 4 | 49 | 230 | 4 | 180 | 1000 |
| 5 | 186 | 700 | 5 | 550 | 3600 |
| 7F | 180 | 680 | 7F | 360 | 4100 |
| 9V | 52 | 520 | 9V/9N | 320/380 | 3300/3800 |
| 9N | — | — | | | |
| 14 | 85 | 400 | 14 | 310 | 32000 |
| 15A | — | — | 15A/15B | 790/900 | 5800/6200 |
| 15B | — | — | | | |
| 18C | 175 | 800 | 18C | 600 | 6800 |
| 22F | — | — | 22F | 1020 | 8150 |
| 23F | 53 | 450 | 23F | 300 | 3200 |

Note:
1VI-18V-3 = 10-monovalent compounds and 4 bivalent compounds mixed together.

Example 10

Table 9 shows immune response with PEG and without PEG covalent compounds.

TABLE 9

13-v comparative IgG Analysis of PEGylated Compounds vs. Conventional Compounds (IgG µg/ml)

| Serotype | PEGylated 13V 2.2 µg/dose | Conventional 13V 2.2 µg/dose | PREVNAR® 13V 2.2 µg/dose | Pneomovax 23V 25 µg/dose |
|---|---|---|---|---|
| 1 | 6.07 | 3.4 | 3.43 | 0.21 |
| 3 | 0.95 | 0.36 | 0.34 | 0.2 |
| 4 | 36.64 | 8.436 | 7.30 | 0.4 |
| 5 | 20.22 | 7.552 | 2.40 | 0.35 |
| 6A | 41.44 | 32.38 | 30.35 | 0.5 |

TABLE 9-continued 13-v comparative IgG Analysis of PEGylated Compounds vs. Conventional Compounds (IgG µg/ml)

| Serotype | PEGylated 13V 2.2 µg/dose | Conventional 13V 2.2 µg/dose | PREVNAR® 13V 2.2 µg/dose | Pneomovax 23V 25 µg/dose |
|---|---|---|---|---|
| 6B | 42.86 | 18.06 | 22.50 | <0.4 |
| 7F | 112.22 | 27.592 | 33.79 | 0.4 |
| 9V | 36.17 | 3.756 | 4.20 | 0.35 |
| 14 | 16.34 | 12.3 | 6.06 | <0.37 |
| 18C | 27.72 | 4.5 | 4.26 | <0.5 |
| 19A | 24.72 | 5.773 | 5.61 | <0.14 |
| 19F | 32.86 | 10.384 | 11.05 | <0.35 |
| 23F | 67.9 | 25.31 | 26.86 | <0.5 |

PEGylated compounds involve PEGylated Bis-hydrazide (1-2 kDa)—HZ-PEG2K-HZ. Conventional means conjugation with CRM197.

Increasing the number of serotype has a detrimental effect on the potencies of the same conjugates when there is an increase in serotypes. This is seen for PREVNAR® 13 compared with PREVNAR® 7.

Surprisingly the use of PEG demonstrates prevention of such an effect and the immune responses remains elevated and the same in spite of an increased number of serotypes.

Example 11 Anti-CRM197 Antibody Response of IVT-25Valent PEGylated. Compounds of 28D Sera Measured and Compared with PREVNAR®-13 28D Sera Anti-CRM197 antibodies were 50% of PREVNAR®-13 antibodies. Although IVT-25 has 25-serotypes compared to the 13 serotypes of PREVNAR®-13, meaning IVT-25 has almost twice the protein content, IVT-25 had 50% less antibodies than PREVNAR®-13. A rise in the numbers or serotypes does not affect the polysaccharide response which is believed due to the PEGylation (see Table 10).

TABLE 10

Total Rabbit IgG Data of IVT-25V and PREVNAR®-13 Individual Rabbit Analysis | GMC

| Serotype | 1 | 3 | 4 | 5 | 6B | 7F | 9V | 14 | 18C | 19A | 19F | 23F |
|---|---|---|---|---|---|---|---|---|---|---|---|---|
| Prevenar 13-28D | 2.54 | 2.49 | 6.08 | 8.38 | 12.98 | 17.86 | 4.49 | 4.03 | 7.51 | 9.64 | 15.79 | 12.88 |
| PCV25V IVT-G3-28D | 9.44 | 3.92 | 11.58 | 19.25 | 25.46 | 39.93 | 13.5 | 31.08 | 13.32 | 21.07 | 29.8 | 23.61 |

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. An immunogenic composition comprising a first group of monovalent capsular polysaccharides and a second group of bivalent or multivalent capsular polysaccharides wherein:
the first group of monovalent capsular polysaccharides comprise polysaccharides of *S. pneumoniae* serotypes 1, 2, 3, 4, 5, 7F, 8, 10A, 11A, 12F, 14, 17F, 18C, 20, 22F, 23F, 24F, 33F and 35B; and
the second group of bivalent or multivalent capsular polysaccharides comprising two or more polysaccharides selected from one or more of the groups consisting of *S. pneumoniae* serotypes 6A/6B/6C/6D, *S. pneumoniae* serotypes 9V/9N/9A/9B, *S. pneumoniae* serotypes 15B/15A/15C, and *S. pneumoniae* serotypes 19A/19F, wherein:
the first group of monovalent capsular polysaccharides are each covalently coupled to a PEG linker and a first carrier protein, and
the second group of bivalent or multivalent capsular polysaccharides are each covalently coupled to another PEG linker and another carrier protein.

2. The composition of claim 1, wherein the bivalent or multivalent capsular polysaccharides comprises two immunologically cross-reactive serotypes of *S. pneumoniae*.

3. The composition of claim 2, wherein the second group of bivalent or multivalent capsular polysaccharides comprises a structure polysaccharide-PEG-carrier protein-PEG-polysaccharide.

4. The composition of claim 2, wherein the bivalent or multivalent capsular polysaccharides are covalently coupled to the another carrier protein sequentially or concurrently.

5. The composition of claim 1, wherein the first group of monovalent capsular polysaccharides and/or the second group of bivalent or multivalent capsular polysaccharides comprise capsular polysaccharides of from about 10 kDa to about 50 kDa, from about 30 KDa to about 100 KDa, and/or from about 100 KDa to about 300 KDa.

6. The composition of claim 1, wherein the second group of bivalent or multivalent capsular polysaccharides comprise the structure 6A-PEG-CRM197-PEG-6B.

7. The composition of claim 1, wherein the first carrier protein and/or the second carrier protein comprises tetanus toxoid, diphtheria toxoid, CRM197, tetanus toxoid fragments (TTHc), *Neisseria meningitidis* protein PorB, RSV virus proteins, *Bordetella pertussis* proteins, Pertussis toxoid (PT), adenylate cyclase toxin (ACT), 69 KDa protein of Hepatitis B virus, Human Papilloma viral protein antigens, Human Papilloma virus virus-like particle (VLP) forms, Hepatitis B virus core antigen, Hepatitis B virus VLP forms, Hepatitis B virus surface antigen (HBsAg), and/or combinations thereof.

8. The composition of claim 1, which comprises 4 micrograms or less of total polysaccharides per dose.

9. The composition of claim 1, wherein the first carrier protein and the second carrier protein comprise from about 0.5% to about 0.8% by weight.

10. The composition of claim 1, which comprises about equal amount by weight of capsular polysaccharides to total carrier protein.

11. The composition of claim 1, which comprises a greater amount by weight of capsular polysaccharides to total carrier protein.

12. The composition of claim 1, further comprising at least one adjuvant.

13. The composition of claim 12, wherein the adjuvant is selected from the group consisting of aluminum salt, calcium phosphate, a liposome of monophosphoryl lipid A (MPLA), saponin QS-21, a TLR7/8 agonist, and combinations thereof.

14. The composition of claim 13, wherein the aluminum salt is selected from the group consisting of aluminum phosphate, aluminum sulfate and aluminum hydroxide.

15. The composition of claim 1, further comprising one or more serotypes of *Haemophilus influenza* type a, *Haemophilus influenza* type b, Group B *Streptococcus, Neisseria meningitis* and/or combinations thereof.

16. The composition of claim 1, further comprising monovalent capsular polysaccharides and/or bivalent and/or multivalent capsular polysaccharides derived from *Haemophilus influenzae* serotypes a/b/c/d/e/f, non-typeable *Haemophilus influenzae* (NTHi) polysaccharides, *Moraxella catarrhalis* Lipooligosaccharides (LOS) and/or combinations thereof.

17. The composition of claim 1, further comprising monovalent capsular polysaccharides and/or bivalent and/or multivalent capsular polysaccharides comprising capsular polysaccharides of *N. meningitis* serotypes A, B, C, Y, W-135 or X.

18. The composition of claim 1, further comprising monovalent capsular polysaccharides and/or bivalent and/or multivalent capsular polysaccharides comprising capsular polysaccharides of Group B *Streptococcus* serotypes Ia, Ib, II, III, IV, V, VI, VII, VIII, IX, or N.

19. The composition of claim 1, wherein the first group of monovalent capsular polysaccharides is approximately equivalent by weight to and/or the second group of bivalent or multivalent capsular polysaccharides.

20. The composition of claim 1, which, upon administration to a subject, generates a lower immune response to carrier protein in comparison to monovalent conjugates comprised of the same capsular polysaccharides.

21. The composition of claim 1, which provides effective treatment for infection by *Streptococcus* bacteria.

22. The composition of claim 1, further comprising a therapeutically effective amount and a pharmacologically acceptable carrier.

23. The composition of claim 1, further comprising capsular polysaccharides of *Haemophilus influenza, N. meningitis,* Group B Streptococcus, and/or combinations thereof.

24. An immunogenic composition comprising a first group of monovalent capsular polysaccharides and a second group of bivalent or multivalent capsular polysaccharides wherein:
the first group of monovalent capsular polysaccharides comprise polysaccharides of *Streptococcus pneumoniae* serotypes 1, 2, 3, 4, 5, 7F, 8, 10A, 11A, 12F, 14, 17F, 18C, 20, 22F, 23F, 24F, 33F and 35B; and
the second group of bivalent or multivalent capsular polysaccharides comprising two or more polysaccharides selected from one or more of the groups consisting of *S. pneumoniae* serotypes 6A, 6B, 6C, and 6D, *S. pneumoniae* serotypes 9A, 9B, 9N, and 9V, *S. pneumoniae* serotypes 15A, 15B, and 15C, and *S. pneumoniae* serotypes 19A and 19F; wherein,
polysaccharides of *S. pneumoniae* serotypes 6A, 6B, 6C, 6D, 9A, 9B, 9N, 9V, 15A, 15B, 15C, 19A, and 19F that are not included in the second group are included in the first group:
the first group of monovalent capsular polysaccharides are each covalently coupled to a first PEG linker which is coupled to a first carrier protein, and the second group of bivalent or multivalent capsular polysaccharides are each covalently coupled to a second PEG linker which is coupled to a second carrier protein.

25. The composition of claim 24, wherein the first group of monovalent capsular polysaccharides comprise polysaccharides of *Streptococcus pneumoniae* serotypes 1, 2, 3, 4, 5, 7F, 8, 10A, 11A, 12F, 14, 15A, 15B, 15C, 17F, 18C, 19A, 19F 20, 22F, 23F, 24F, 33F and 35B, and the second group of bivalent or multivalent capsular polysaccharides comprises polysaccharides of *S. pneumoniae* serotypes 6A, 6B, 6C, 6D, 9A, 9B, 9N, and 9V.

26. The composition of claim 24, wherein the first group of monovalent capsular polysaccharides comprise polysaccharides of *Streptococcus pneumoniae* serotypes 1, 2, 3, 4, 5, 7F, 8, 9A, 9B, 9N, 9V, 10A, 11A, 12F, 14, 17F, 18C, 19A, 19F, 20, 22F, 23F, 24F, 33F and 35B, and the second group of bivalent or multivalent capsular polysaccharides comprises polysaccharides of *S. pneumoniae* serotypes 6A, 6B, 6C, 6D, 15A, 15B, and 15C.

27. The composition of claim 24, wherein the first group of monovalent capsular polysaccharides comprise polysaccharides of *Streptococcus pneumoniae* serotypes 1, 2, 3, 4, 5, 7F, 8, 9A, 9B, 9N, 9V, 10A, 11A, 12F, 14, 15A, 15B, 15C, 17F, 18C, 20, 22F, 23F, 24F, 33F and 35B, and the second group of bivalent or multivalent capsular polysaccharides comprises polysaccharides of *S. pneumoniae* serotypes 6A, 6B, 6C, 6D, 19A, and 19F.

28. The composition of claim 24, wherein the first group of monovalent capsular polysaccharides comprise polysaccharides of *Streptococcus pneumoniae* serotypes 1, 2, 3, 4, 5, 6A, 6B, 6C, 6D, 7F, 8, 10A, 11A, 12F, 14, 17F, 18C, 19A, 19F, 20, 22F, 23F, 24F, 33F and 35B, and the second group of bivalent or multivalent capsular polysaccharides comprises polysaccharides of *S. pneumoniae* serotypes 9A, 9B, 9N, 9V, 15A, 15B, and 15C.

29. The composition of claim 24, wherein the first group of monovalent capsular polysaccharides comprise polysaccharides of *Streptococcus pneumoniae* serotypes 1, 2, 3, 4, 5, 6A, 6B, 6C, 6D, 7F, 8, 10A, 11A, 12F, 14, 15A, 15B, 15C, 17F, 18C, 20, 22F, 23F, 24F, 33F and 35B, and the second group of bivalent or multivalent capsular polysaccharides comprises polysaccharides of *S. pneumoniae* serotypes 9A, 9B, 9N, 9V, 19A, and 19F.

30. The composition of claim 24, wherein the first group of monovalent capsular polysaccharides comprise polysaccharides of *Streptococcus pneumoniae* serotypes 1, 2, 3, 4, 5, 6A, 6B, 6C, 6D, 7F, 8, 9A, 9B, 9N, 9V, 10A, 11A, 12F, 14, 17F, 18C, 20, 22F, 23F, 24F, 33F and 35B, and the second group of bivalent or multivalent capsular polysaccharides comprises polysaccharides of *S. pneumoniae* serotypes 15A, 15B, 15C, 19A, and 19F.

31. The composition of claim 24, wherein the first group of monovalent capsular polysaccharides comprise polysaccharides of *Streptococcus pneumoniae* serotypes 1, 2, 3, 4, 5, 7F, 8, 10A, 11A, 12F, 14, 17F, 18C, 20, 22F, 23F, 24F, 33F and 35B, and the second group of bivalent or multivalent capsular polysaccharides comprises polysaccharides of *S. pneumoniae* serotypes 6A, 6B, 6C, 6D, 9A, 9B, 9N, 9V, 15A, 15B, 15C, 19A, and 19F.

32. The composition of claim 24, wherein the first group of monovalent capsular polysaccharides and/or the second group of bivalent or multivalent capsular polysaccharides comprise capsular polysaccharides of from about 10 kDa to about 50 kDa, from about 30 KDa to about 100 KDa, and/or from about 100 KDa to about 300 KDa.

33. The composition of claim 24, which comprises 4 micrograms or less of total polysaccharides per dose.

34. The composition of claim 24, wherein the first carrier protein and the second carrier protein comprise from about 0.5% to about 0.7% by weight.

35. The composition of claim 24, which comprises about equal amount by weight of capsular polysaccharides to total carrier protein.

36. The composition of claim 24, which comprises a greater amount by weight of capsular polysaccharides to total carrier protein.

* * * * *